US009944942B2

(12) United States Patent
Luo et al.

(10) Patent No.: US 9,944,942 B2
(45) Date of Patent: Apr. 17, 2018

(54) METHODS AND COMPOSITIONS FOR ENHANCED RESISTANCE TO ABIOTIC STRESS IN PLANTS

(71) Applicant: Clemson University, Clemson, SC (US)

(72) Inventors: Hong Luo, Clemson, SC (US); Dayong Li, Beijing (CN); Man Zhou, Central, SC (US); Qian Hu, Clemson, SC (US)

(73) Assignee: CLEMSON UNIVERSITY, Anderson, SC (US)

( * ) Notice: Subject to any disclaimer, the term of this patent is extended or adjusted under 35 U.S.C. 154(b) by 1018 days.

(21) Appl. No.: 13/672,320

(22) Filed: Nov. 8, 2012

(65) Prior Publication Data

US 2013/0117882 A1 May 9, 2013

Related U.S. Application Data

(60) Provisional application No. 61/556,852, filed on Nov. 8, 2011.

(51) Int. Cl.
*C12N 15/11* (2006.01)
*C12N 15/13* (2006.01)
*C12N 15/82* (2006.01)
*A01H 5/00* (2018.01)

(52) U.S. Cl.
CPC .......... *C12N 15/8273* (2013.01); *C12N 15/11* (2013.01); *C12N 15/8218* (2013.01); *C12N 15/8271* (2013.01)

(58) Field of Classification Search
CPC .................................. C12N 15/8273
See application file for complete search history.

(56) References Cited

U.S. PATENT DOCUMENTS 8,946,511 B2 * 2/2015 Allen ................ C12N 15/8216
536/24.5
2006/0123505 A1 * 6/2006 Kikuchi ............... C07K 14/415
800/278

OTHER PUBLICATIONS

Davletona et al (Plant Physiology, Oct. 2005, vol. 139, pp. 847-856).*
Sunkar et al (The Plant Cell, vol. 16, 2001-2019, Aug. 2004).*
Palatnik et al (Developmental Cell 13, 115-125, Jul. 2007).*
MiRBase Accession No. MIMAT0020914 (2004).*
Lv et al (Gene 459 (2010) 39-47).*
Thiebaut (Plant, Cell and Environment (2012) 35, 502-512—first published online on Oct. 23, 2011).*
Liu et al (RNA (2008) 14: 836-843).*
Cai et al (Genomics and Applied Biology (2010) vol. 29, No. 4. 804-808).*
Cai et al (Genomics and Applied Biology (2010) vol. 29, No. 4. 804-808) (Year: 2010).*
Addo-Quaye et al. "Sliced microRNA targets and precise loop-first processing of MIR319 hairpins revealed by analysis of the Physcomitrella patens degradome", RNA, 2009, 15:2112-2121.
Bologna et al. "A loop-to-base processing mechanism underlies the biogenesis of plant microRNAs miR319 and miR159", The EMBO Journal, 2009, 28:3646-3656.
Gao et al. "osa-MIR393: a salinity- and alkaline stress-related microRNA gene", Mol Biol Rep (2011) 38:237-242.
Gao et al. "Over-expression of osa-MIR396c decreases salt and alkali stress tolerance", Planta, 2010, 231:991-1001.
Kong et al. "Differential Expression of microRNAs in Maize Inbred and Hybrid Lines during Salt and Drought Stress", American Journal of Plant Sciences, 2010, 1:69-76.
Koyama et al. "TCP Transcription Factors Regulate the Activities of Asymmetric LEAVES1 and miR164, as Well as the Auxin Response, during Differentiation of Leaves in Arabidopsis", Plant Cell, 2010, 22:3574-3588.
Li et al. "Evolution of MIR159/319 microRNA genes and their post-transcriptional regulatory link to siRNA pathways", BMC Evolutionary Biology, 2011, 11:122.
Liu et al. "Microarray-based analysis of stress-regulated microRNAs in Arabidopsis thaliana", RNA, 2008, 14:836-843.
Mao et al. "miR319a-targeted BrpTCP genes modulate head shape in Brassica rapa by differential cell division arrest in leaf regions", Plant Physiology Preview, Published on Dec. 18, 2013, 47 pages.
Nag et al. "miR319a targeting of TCP4 is critical for petal growth and development in Arabidopsis", PNAS, Dec. 29, 2009, vol. 106, No. 52, 22534-22539.
Naqvi et al. "MicroRNA profiling of tomato leaf curl new delhi virus (tolcndv) infected tomato leaves indicates that deregulation of mir159,319 and mir172 might be linked with leaf curl disease", Virology Journal, 2010, 7:281.
Nath et al. "Genetic Control Surface Curvature", Science, Feb. 2003, vol. 299.
Ori et al. "Regulation of LANCEOLATE by mirR319 is required for compound-leaf development in tomato", Nature Genetics, vol. 39, No. 6, Jun. 2007.
Palatnik et al. "Control of leaf morphogenesis by microRNAs", Nature, Aug. 20, 2003, 7 pages.
Schommer et al. "Control of Jasmonate Biosynthesis and Senescence by miR319 Targets", PLOS Biology, Sep. 2008, vol. 6, Issue 9, e230, pp. 1991-2001.
Thiebaut et al. "Regulation of miR319 during cold stress in sugarcane", Plant, Cell & Environment, Accepted Article, Sep. 9, 2011, 39 Pages.

(Continued)

Primary Examiner — Lee A Visone
(74) Attorney, Agent, or Firm — Myers Bigel, P.A.

(57) ABSTRACT

The present invention provides transgenic plants having increased tolerance to abiotic stress comprising a recombinant nucleic acid molecule, said recombinant nucleic acid molecule comprising a nucleotide sequence encoding miR319 operatively associated with a promoter, a nucleotide sequence that is antisense to a portion of consecutive nucleotides of a nucleotide sequence encoding PCF5, and/or a nucleotide sequence that encodes a portion of consecutive nucleotides of a nucleotide sequence encoding PCF5, which when expressed produces an antisense nucleotide sequence, wherein expression of the nucleotide sequence confers increased tolerance to abiotic stress. Also provided are methods and compositions for making said transgenic plants.

7 Claims, 29 Drawing Sheets

(56) References Cited

OTHER PUBLICATIONS

Wesley et al. "Construct design for efficient, effective and high-throughput gene silencing in plants", *The Plant Journal*, 2001, 27(6), 581-590.

Yang et al. Overexpression of microRNA319 impacts leaf morphogenesis and leads to enhanced cold tolerance in rice (*Oryza sativa* L.), *Plant, Cell and Environment*, 2013, 36:2207-2218.

Yao et al. "Genome-Wide Comparative Analysis and Expression Pattern of TCP Gene Families in *Arabidopsis thaliana* and *Oryza sativa*", *Journal of Integrative Plant Biology*, 2007, 49 (6):885-897.

Zhang et al. "Over-expression of microRNA169 confers enhanced drought tolerance to tomato", *Biotechnol Lett.*, 2011, 33:403-409.

Zhou et al. "Constitutive Expression of a miR319 Gene Alters Plant Development and Enhances Salt and Drought Tolerance in Transgenic Creeping Bentgrass", *Plant Physiology*, Mar. 2013, vol. 161, pp. 1375-1391.

Zhou et al. "Genome-wide identification and analysis of drought-responsive microRNAs in *Oryza sativa*", *Journal of Experimental Botany*, vol. 61, No. 15, pp. 4157-4168, 2010.

Khraiwesh et al. "Role of miRNAs and siRNAs in biotic and abiotic stress responses of plants", *Biochim Biophys Acta*, Feb. 2012, 1819(2):137-148, ePub May 13, 2011), 26 pages.

Yuan et al. "Constitutive Expression of Rice MicroRNA528 Alters Plant Development and Enhances Tolerance to Salinity Stress and Nitrogen in Starvation in Creeping Bentgrass", *Plant Physiology*, Sep. 2015, vol. 169, pp. 576-593.

Huang "Rice NAC transcription factor ONAC095 plays opposite roles in drought and cold stress tolerance", *BMC Plant Biology*, 15:203, 18 pages (2016).

Liu et al. "AtPUB19, a U-Box E3 Ubiquitin Ligase, Negatively Regulates Abscisic Acid an Drought Responses in *Arabidopsis thaliana*", *Molecular Plant*, 4(6) pp. 938-946 (2011).

Seo et al. "Roles of Four *Arabidopsis* U-Box E3 Ubiquitin Ligases in Negative Regulation of Abscisic Acid-Mediated Drought Stress Responses1[C][W][OA]". *Plant Physiology*, 160, pp. 556-568 (2012).

Wang, Q, et al. "Heat stress-induced BBX18 negatively regulates the thermotolerance in *Arabidopsis*", *Mol Biol Rep*, 40, pp. 2679-2688 (2013).

Zhang et al. "Overexpression of GASA5 increases the sensitivity of *Arabidopsis* to heat stress", *J. Plant Physiol.*, 168, pp. 2093-2101 (2011).

* cited by examiner

A

B

C

RT-PCR

D

A

B

C

D

E

F

G

A

B

C

D

E

F

G

A

B

Six days after 200 mM NaCl treatment

A

B

C

Days after water withholding

A

B

C

D

E

A

B

Days after water withholding

A

B

A

B

C

RT-PCR with RNA from wild-type shoots

SEQUENCE LISTING

```
<160> NUMBER OF SEQ ID NOS: 18

<210> SEQ ID NO 1
<211> LENGTH: 1540
<212> TYPE: DNA
<213> ORGANISM: Oryza sativa

<400> SEQUENCE: 1
agagccatgg cattgctcct tgcctccttc cagcttctcc ttcagttcca ggccgatagc      60
cagttaaacc caaatataca tctgctcttt cttttgcccg gttacagcgt agcttctctc     120
aatgctttgc ccccctcatt ccatttatgt tttattcctg tcatcttcgt gacctagtta     180 gtttccttt ctttgccgcg ttgtttaaga tttccattgt atttcttgtt ttgcaattca      240
tttggtgctc caagattgtg gctttgacta catgtgtaag aagagagctc tcttcagtcc     300
actctcagat ggctgtaggg ttttattagc tgccgaatca tccattcacc taccaggaaa     360
gttgcaggag tgtatctctt ggtagcggac tggatgacgc gggagctaaa atttagctct     420
gcgccgtttg tggttggact gaagggtgct cccttgctca agcactcgtg cataaaatca     480
tgccctaatg ttaataataa tcttcagatt tctatatgag ttttatgtcc agtgtgttca     540
gtttcaagat ttggactttt tttttatatc agtggtcaat gacctgggaa atctacagac     600
agaaatctac tgaagcattg actagactat ccaagcctgt ctggatatgg cttgtcatca     660
acagtgcttt catcattctt aagctgtatc tactgaagta tgatttgatt cggtttgtgt     720
ttttactata ctggtgagga aggaatatat gtccccaact gtatgctgtt attgtacata     780
caatattcag ggtgtgttta gttcacgcta aaacttaaag tttagttaaa attggaacga     840
tgtgatggaa aagttgaaag tttgtgtgta agaaagtttt aatgtgatag aaaagttgga     900
agtttgaaga aaaagtttga aagtaaactc ggcctcagtt caaaactaca ggcatgtaaa     960
gcattattag ttaaaaatgt caacgttaac attattgtaa atgtgtctat gcatggaaat    1020
ctctttattc acatcctgcg gcccgtacat attgcataag tgctcagatt accacgaggc    1080
ctagaaggtt ttactgagat cattgccgaa atccgctttc aggggcagct agccagctaa    1140
acattgactt tctgttactc agattcttca ggtcagttaa ttcagaagtt ggcagtttgt    1200
taatgaattc tcttacggca ttctgtaact agctagctat tgtataaatt aagacctata    1260
tttaatttac tatttgggta gagatcgatg agttatattt gtgtaaagag tgattggatc    1320
tactatctct aggatctgtt gtagggaatt aaacgcaact tcaaggatta gtggtgctta    1380
catgcatgca tgcacattgg acacattgag attgatctgt tgtatacatc atcagaggag    1440
gatgtaaacc cagaggacat atactagtac tatatggtta aggatggctt tcccggaaca    1500
tatatatcaa attagcaatc atgtagtatt tttcttttgc                          1540
```

<210> SEQ ID NO 2
<211> LENGTH: 179
<212> TYPE: RNA
<213> ORGANISM: Oryza sativa

<400> SEQUENCE: 2
uguguaagaa gagagcucuc uucaguccac ucucagaugg cuguaggguu uuauuagcug    60
ccgaaucauc cauucaccua ccaagaaagu gcaggagug uaucucuugg uagcggacug    120
gaugacgcgg gagcuaaaau uuagcucugc gccguuugug guuggacuga agggugcuc    179

<210> SEQ ID NO 3
<211> LENGTH: 179
<212> TYPE: RNA
<213> ORGANISM: Oryza sativa

<400> SEQUENCE: 3
gauggaugga agagagcguc cuucaguucca cucaugggcg gugcuagggu cgaauuagcu    60
gccgacucau ucacccacau gccaagcaag aaacgcuuga gauagcgaag cuuagcagau    120
gagugaauga agcgggaggu aacguuccga ucucgcgccg ucuuugcuug gacugaagg    179

<210> SEQ ID NO 4
<211> LENGTH: 859
<212> TYPE: DNA
<213> ORGANISM: Agrostis stolonifera

<400> SEQUENCE: 4
ccgccgagaa cttcgacgac caggcgcttg ctatcacgat cgcgcatgcc tcgttcgact    60
tcgccggctc ttctggcagc ggaggagcca ccggcggcat cagcttcctg ccgccgtcgc    120
tggactcgga ctccatagcc gacacgatca agtccttctt ccccatgggc ggcaccgcag    180
gaggagaggc gtcgtcatcc actgtggcgg ctcactcgtc ggccatgagt ttccagagct    240
acacaccgga cctcttgtcg cgcaccggca gccagagcca agaactccgg ctgtcgctgc    300
agcctttacc agaccccatg tttcaccacc agcagcacca gcagcagcag gagcagcaca    360
ggtcgcacgg ccacgacagc aacggcaccg cgcagcaggc gatcttcccc ggcggcgcca    420
attactcatt tggcggcggc gtcatgtggg gagagcaggc gcaggcccag cgcatgttgc    480
cgtggagcgt gcccgaccca ggcggtggcg gcggagcac tggcggctac ttgttcaacg    540
tgtcgcagca ggcggcgcat atgcaggcgg cgctcagtgg ccagagccag ttcttcttcc    600
agaggggacc ccttcagtcc agtaaccagc cctccgaccg aggatggccg gagaccgtcg    660
aagctgacaa cagcaactcg atgcagcagc agcaccacca ccaagggggc ttgaacccctt    720 ccgtgtccgc cgcaatcggg ttcgctcctg gcgtcagctt ctccggattc cgcctccccg    780
cgaggataca gggcgacgag gagcacaacg gcggcaatgg cgacaagccg ccgtccgtct    840
cctcggcttc tcaccactg                                                 859

<210> SEQ ID NO 5
<211> LENGTH: 23
<212> TYPE: DNA
<213> ORGANISM: Artificial
<220> FEATURE:
<223> OTHER INFORMATION: PCR primer

<400> SEQUENCE: 5
tctagaagag ccatggcatt gct                                            23

<210> SEQ ID NO 6
<211> LENGTH: 31
<212> TYPE: DNA
<213> ORGANISM: Artificial
<220> FEATURE:
<223> OTHER INFORMATION: PCR primer

<400> SEQUENCE: 6
gtcgacgcaa aagaaaaata ctacatgatt g        31

<210> SEQ ID NO 7
<211> LENGTH: 20
<212> TYPE: RNA
<213> ORGANISM: Oryza sativa

<400> SEQUENCE: 7
uuggacugaa gggugcuccc        20

<210> SEQ ID NO 8
<211> LENGTH: 748
<212> TYPE: DNA
<213> ORGANISM: Panicum virgatum

<400> SEQUENCE: 8
ggatataatc tgaggtgttc tattggtagc ccaacacatg cggaccggaa gcaaaaatct        60
catcaagcac tgatttgaaa tgttgttcat gttgacaatt tacgcagaca tgcttctact       120
ttaatacatc ttgaaaatat gagcacagaa tttggagata gcagacacac accaacatac       180
atcaggaaaa aatcaagctg tgagtggaat tatatacagc tgaaaaatgt aaagatatc        240
tgttattgag aaacatctcc tggctgcccg gataagtcca gcataaaaga ttgaaagtga       300
acctgaaagc atacatatat agttcatgac accctgcaga ttaatttctt ttagaaatga       360
aatttaaaat ctcgagagct cgaacagcaa gagaaatcga agcaagattg ttctatcaaa       420
cataagtgag gtcaagaatc ttgttcgttc aagagcctca gagcttatca aaagtaaaga       480
gagattaaag taactcaaga tcggcatcga ggtagattat ttcatgcacg agcaagggag       540
caccccttcag tccaaccaca aacagcgtag agcttaatt tagctcccgc gccatccaat        600
cagctaccaa gacattccgc gtccatggat cttgggtagg tgaatggatg agtcggcagc       660
taatgaaccc tacggccatt tcagagtgga ctgaagagag ctctcttcca gagaagccat       720
aaactcaaaa aaccaactca gatgaaca        748

<210> SEQ ID NO 9
<211> LENGTH: 58
<212> TYPE: PRT
<213> ORGANISM: Oryza sativa

<400> SEQUENCE: 9

Lys Asp Arg His Ser Lys Val Cys Thr Ala Arg Gly Pro Arg Asp Arg
1               5                   10                  15

Arg Val Arg Leu Ser Ala His Thr Ala Ile Gln Phe Tyr Asp Val Gln
                20                  25                  30

Asp Arg Leu Gly Tyr Asp Arg Pro Ser Lys Ala Val Asp Trp Leu Ile
            35                  40                  45

Lys Asn Ala Lys Asp Ala Ile Asp Lys Leu
        50                  55

<210> SEQ ID NO 10
<211> LENGTH: 15

```
<212> TYPE: PRT
<213> ORGANISM: Artificial
<220> FEATURE:
<223> OTHER INFORMATION: Consensus Motif 3 sequence

<400> SEQUENCE: 10

Gly Cys Gly Glu Ile Val Glu Val Gln Gly Gly His Ile Val Arg
1               5                   10                  15

<210> SEQ ID NO 11
<211> LENGTH: 22
<212> TYPE: PRT
<213> ORGANISM: Artificial
<220> FEATURE:
<223> OTHER INFORMATION: COnsensus Motif 6 sequence

<400> SEQUENCE: 11

Ser Phe Leu Pro Pro Ser Met Asp Ser Asp Ser Ile Ala Asp Thr Ile
1               5                   10                  15

Lys Ser Phe Phe Pro Val
            20

<210> SEQ ID NO 12
<211> LENGTH: 8
<212> TYPE: PRT
<213> ORGANISM: Artificial
<220> FEATURE:
<223> OTHER INFORMATION: Consensus Motif 12 sequence

<400> SEQUENCE: 12

Arg Gly Thr Leu Gln Ser Asn Tyr
1               5

<210> SEQ ID NO 13
<211> LENGTH: 458
<212> TYPE: PRT
<213> ORGANISM: Oryza sativa

<400> SEQUENCE: 13

Met Gly Asp Ala Gly Gly His Ser His His Gln His Gly Phe Gln
1               5                   10                  15

Pro Gln Leu Leu Ser Phe Gly Gly Val Gly His His His His Leu His
                20                  25                  30

Gln Phe Thr Ala Gln Pro Gln Pro Ala Ala Ser His Thr Arg Gly
                35                  40                  45

Arg Gly Gly Gly Gly Glu Ile Val Pro Ala Thr Thr Thr Pro Arg Ser
    50                  55                  60

Arg Gly Gly Gly Gly Gly Gly Gly Glu Ile Val Ala Val Gln Gly
65              70                  75                  80

Gly His Ile Val Arg Ser Thr Gly Arg Lys Asp Arg His Ser Lys Val
                85                  90                  95

Cys Thr Ala Arg Gly Pro Arg Asp Arg Arg Val Arg Leu Ser Ala His
                100                 105                 110

Thr Ala Ile Gln Phe Tyr Asp Val Gln Asp Arg Leu Gly Tyr Asp Arg
                115                 120                 125

Pro Ser Lys Ala Val Asp Trp Leu Ile Lys Asn Ala Lys Asp Ala Ile
            130                 135                 140

Asp Lys Leu Asp Val Leu Pro Ala Trp Gln Pro Thr Ala Gly Ala
145                 150                 155                 160

Gly Ala Gly Asn Ala Ala Ala Pro Pro Ser Ser Thr His Pro Asp
                165                 170                 175
```

Ser Ala Glu Asn Ser Asp Asp Gln Ala Gln Ala Ile Thr Val Ala His
            180                 185                 190

Thr Ala Phe Asp Phe Ala Gly Gly Ser Gly Gly Thr Ser Phe Leu
            195                 200                 205

Pro Pro Ser Leu Asp Ser Asp Ala Ile Ala Asp Thr Ile Lys Ser Phe
210                 215                 220

Phe Pro Met Gly Gly Thr Ala Gly Gly Glu Ala Ser Ser Ser Thr Thr
225                 230                 235                 240

Ala Ala Gln Ser Ser Ala Met Gly Phe Gln Ser Tyr Thr Pro Asp Leu
            245                 250                 255

Leu Ser Arg Thr Gly Ser Gln Ser Gln Glu Leu Arg Leu Ser Leu Gln
            260                 265                 270

Ser Leu Pro Asp Pro Met Phe His His Gln His Arg His Gly Gly
            275                 280                 285

Gly Gly Gly Gly Gly Asn Gly Thr Thr Gln Gln Ala Leu Phe Ser Gly
            290                 295                 300

Ala Ala Asn Tyr Ser Phe Gly Gly Gly Ala Met Trp Ala Thr Glu Gln
305                 310                 315                 320

Gln Ala Gln Asn Gln Arg Met Leu Pro Trp Asn Val Pro Asp Pro Gly
            325                 330                 335

Gly Gly Gly Gly Ala Ala Tyr Leu Phe Asn Val Ser Gln Gln Ala Ala
            340                 345                 350

His Met Gln Ala Ala Ala Ala Leu Gly Gly His Gln Ser Gln Phe
            355                 360                 365

Phe Phe Gln Arg Gly Pro Leu Gln Ser Ser Asn Gln Pro Ser Glu Arg
            370                 375                 380

Gly Trp Pro Glu Thr Val Glu Ala Asp Asn Gln Met Ser His His Gln
385                 390                 395                 400

Gly Gly Leu Ser Pro Ser Val Ser Ala Ala Ile Gly Phe Ala Ala Pro
            405                 410                 415

Gly Ile Gly Phe Ser Gly Phe Arg Leu Pro Ala Arg Ile Gln Gly Asp
            420                 425                 430

Glu Glu His Asn Gly Gly Gly Gly Asn Gly Asp Lys Pro Pro Pro
            435                 440                 445

Pro Ser Ser Val Ser Ser Ala Ser His His
    450                 455

<210> SEQ ID NO 14
<211> LENGTH: 285
<212> TYPE: PRT
<213> ORGANISM: Agrostis stolonifera

<400> SEQUENCE: 14

Ala Glu Asn Phe Asp Asp Gln Ala Leu Ala Ile Thr Ile Ala His Ala
1               5                   10                  15

Ser Phe Asp Phe Ala Gly Ser Ser Gly Ser Gly Gly Ala Thr Gly Gly
            20                  25                  30

Ile Ser Phe Leu Pro Pro Ser Leu Asp Ser Asp Ser Ile Ala Asp Thr
            35                  40                  45

Ile Lys Ser Phe Phe Pro Met Gly Gly Thr Ala Gly Gly Glu Ala Ser
        50                  55                  60

Ser Ser Thr Val Ala Ala His Ser Ser Ala Met Ser Phe Gln Ser Tyr
65                  70                  75                  80

Thr Pro Asp Leu Leu Ser Arg Thr Gly Ser Gln Ser Gln Glu Leu Arg

```
                        85                  90                  95
Leu Ser Leu Gln Pro Leu Pro Asp Pro Met Phe His His Gln Gln His
            100                 105                 110

Gln Gln Gln Gln Glu Gln His Arg Ser His Gly His Asp Ser Asn Gly
        115                 120                 125

Thr Ala Gln Gln Ala Ile Phe Pro Gly Gly Ala Asn Tyr Ser Phe Gly
    130                 135                 140

Gly Gly Val Met Trp Gly Glu Ala Gln Ala Gln Arg Met Leu Pro
145                 150                 155                 160

Trp Ser Val Pro Asp Pro Gly Gly Gly Gly Ser Thr Gly Tyr
                165                 170                 175

Leu Phe Asn Val Ser Gln Gln Ala Ala His Met Gln Ala Ala Leu Ser
                180                 185                 190

Gly Gln Ser Gln Phe Phe Phe Gln Arg Gly Pro Leu Gln Ser Ser Asn
            195                 200                 205

Gln Pro Ser Asp Arg Gly Trp Pro Glu Thr Val Glu Ala Asp Asn Ser
    210                 215                 220

Asn Ser Met Gln Gln Gln His His His Gln Gly Gly Leu Asn Pro Ser
225                 230                 235                 240

Val Ser Ala Ala Ile Gly Phe Ala Pro Gly Val Ser Phe Ser Gly Phe
                245                 250                 255

Arg Leu Pro Ala Arg Ile Gln Gly Asp Glu Glu His Asn Gly Gly Asn
            260                 265                 270

Gly Asp Lys Pro Pro Ser Val Ser Ser Ala Ser His His
        275                 280                 285

<210> SEQ ID NO 15
<211> LENGTH: 15
<212> TYPE: PRT
<213> ORGANISM: Oryza sativa

<400> SEQUENCE: 15

Gly Gly Gly Glu Ile Val Ala Val Gln Gly Gly His Ile Val Arg
1               5                   10                  15

<210> SEQ ID NO 16
<211> LENGTH: 22
<212> TYPE: PRT
<213> ORGANISM: Oryza sativa

<400> SEQUENCE: 16

Ser Phe Leu Pro Pro Ser Leu Asp Ser Asp Ala Ile Ala Asp Thr Ile
1               5                   10                  15

Lys Ser Phe Phe Pro Met
            20

<210> SEQ ID NO 17
<211> LENGTH: 22
<212> TYPE: PRT
<213> ORGANISM: Agrostis stolonifera

<400> SEQUENCE: 17

Ser Phe Leu Pro Pro Ser Leu Asp Ser Asp Ser Ile Ala Asp Thr Ile
1               5                   10                  15

Lys Ser Phe Phe Pro Met
            20

<210> SEQ ID NO 18
```

```
<211> LENGTH: 8
<212> TYPE: PRT
<213> ORGANISM: Oryza sativa

<400> SEQUENCE: 18

Arg Gly Pro Leu Gln Ser Ser Asn
1               5
```

METHODS AND COMPOSITIONS FOR ENHANCED RESISTANCE TO ABIOTIC STRESS IN PLANTS

STATEMENT OF PRIORITY

This application claims the benefit, under 35 U.S.C. § 119 (e), of U.S. Provisional Application No. 61/556,852, filed Nov. 8, 2011, the entire contents of which are incorporated by reference herein.

STATEMENT OF GOVERNMENT SUPPORT

The present invention was made with government support under grant numbers SC-1700315, 2005-39454-16511, 2007-33522-18489, and 2010-33522-21656 awarded by the United States Department of Agriculture National Institute of Food and Agriculture. The United States Government has certain rights in this invention.

STATEMENT REGARDING ELECTRONIC FILING OF A SEQUENCE LISTING

A Sequence Listing in ASCII text format, submitted under 37 C.F.R. § 1.821, entitled 9662-17 ST25.txt, 14,486 bytes in size, generated on Nov. 1, 2012 and filed via EFS-Web, is provided in lieu of a paper copy. This Sequence Listing is hereby incorporated by reference into the specification for its disclosures.

FIELD OF INVENTION

The present invention relates to methods and compositions for producing transgenic plants with enhanced resistance to abiotic stress.

BACKGROUND

Abiotic stress results in significant reductions in crop yield and quality world-wide. Drought, ozone, salinity, toxic metals and extremes in temperature are just a few of the examples of the types of abiotic stresses to which plants are exposed. Two of these stresses, drought and salinity, are widespread in many regions. It is estimated that by the year 2050, more than 50% of all arable lands will be severely affected by salinity. In the face of a global scarcity of water resources and the increased salinization of soil, plant biotechnologies aimed at genetically improving plants to enhance their adaptation to environmental stresses need to be identified and implemented.

In recent years, with the significant advances made in the area of genomics, genetic regulators related to plant stress tolerance have been identified, which may have the potential to be utilized in crop improvement through genetic engineering. One example of such genetic regulators are microRNAs (miRNAs). MicroRNAs are a class of noncoding small RNAs which originate from pri-miRNA transcripts that are encoded by miRNA genes. The pri-miRNA transcripts are processed into smaller 19-24 nucleotide RNAs, which can regulate gene expression, for example, through silencing reactions by translational inhibition or cleavage.

The present invention provides methods and compositions employing miRNAs and small interfering RNAs (siRNA) to enhance abiotic tolerance in plants.

SUMMARY OF THE INVENTION

In one aspect of the invention, a recombinant nucleic acid molecule is provided, the recombinant nucleic acid molecule comprising at least one nucleotide sequence, wherein the at least one nucleotide sequence is: (a) a nucleotide sequence of SEQ ID NO:4; (b) a nucleotide sequence having at least 90% sequence identity to the nucleotide sequence of (a); (c) a nucleotide sequence which anneals under stringent hybridization conditions to the nucleotide sequence of (a) or (b); (d) a nucleotide sequence that differs from the nucleotide sequences of (a), (b) or (c) above due to the degeneracy of the genetic code; or (e) any combination of the nucleotide sequences of (a)-(d).

In a second aspect, the present invention provides a transgenic plant having increased tolerance to abiotic stress comprising a recombinant nucleic acid molecule, said recombinant nucleic acid molecule comprising a nucleotide sequence encoding miR319 operatively associated with a promoter, wherein overexpression of the nucleotide sequence confers increased tolerance to abiotic stress as compared to a plant lacking said recombinant nucleic acid molecule.

In a third aspect, the present invention provides a transgenic plant having increased tolerance to abiotic stress comprising a recombinant nucleic acid molecule, said recombinant nucleic acid molecule comprising: (a) a nucleotide sequence that is antisense to a portion of consecutive nucleotides of a nucleotide sequence encoding PCF5, and/or (b) a nucleotide sequence that encodes a portion of consecutive nucleotides of a nucleotide sequence encoding PCF5, which when expressed produces an antisense nucleotide sequence, wherein the antisense nucleotide sequence confers increased tolerance to abiotic stress as compared to a plant lacking said recombinant nucleic acid molecule.

In a fourth aspect, a transgenic plant having increased tolerance to abiotic stress is provided comprising a recombinant nucleic acid molecule, said recombinant nucleic acid molecule comprising: (a) a nucleotide sequence that is antisense to a portion of consecutive nucleotides of the nucleotide sequence of SEQ ID NO:4 (e.g., about 21 consecutive nucleotides to about to 859 consecutive nucleotides), and/or (b) a nucleotide sequence that encodes a portion of consecutive nucleotides of the nucleotide sequence of SEQ ID NO:4 (e.g., about 21 consecutive nucleotides to about to 859 consecutive nucleotides) which when expressed produces an antisense nucleotide sequence, wherein expression of the antisense nucleotide sequence confers increased tolerance to abiotic stress as compared to a plant lacking said recombinant nucleic acid molecule.

In a fifth aspect of the invention, a method of producing a transgenic plant having increased tolerance to abiotic stress is provided, comprising: a) transforming a plant cell with a recombinant nucleic acid molecule, said recombinant nucleic acid molecule comprising a nucleotide sequence selected from the group consisting of: (i) a nucleotide sequence encoding miR319 operatively associated with a promoter; (ii) a nucleotide sequence that is antisense to a portion of consecutive nucleotides of a nucleotide sequence encoding PCF5, and/or (iii) a nucleotide sequence that encodes a portion of consecutive nucleotides of a nucleotide sequence encoding PCF5, which when expressed produces an antisense nucleotide sequence, to produce a transformed plant cell; and b) regenerating a transgenic plant from the transformed plant cell, thereby producing a transgenic plant having increased tolerance to abiotic stress as compared to a plant lacking said recombinant nucleic acid molecule.

These and other aspects of the invention are set forth in more detail in the description of the invention below.

BRIEF DESCRIPTION OF THE DRAWINGS

FIGS. 1A-1D show the generation and molecular analysis of transgenic lines expressing osmiR319a. FIG. 1A shows the osmiR319a overexpression gene construct, p35S-hyg/actin-osmiR319a, in which the osmiR319a gene is under the control of the rice actin promoter and a CaMV35S promoter-driven hyg gene is included to provide hygromycin resistance for selection. FIG. 1B shows PCR analysis of transgenic plants. FIG. 1C shows RT-PCR analysis of the primary osmiR319a transcripts in the transgenic plants. FIG. 1D shows stem-loop RT analysis of the mature osmiR319a in transgenics.

FIGS. 2A-2I show the morphological changes in the transgenic plants overexpressing osmiR319a. FIG. 2A shows the general morphology of a wild-type (WT) plant and transgenic (TG) plant. FIG. 2B shows a view of a leaf and stem of a WT and TG plant. FIG. 2C shows a sectioning image of WT and TG plant leaves. FIG. 2D shows the leaf blade width in WT and TG plants. FIG. 2E shows the total vein number in WT and TG plants. FIG. 2F shows leaf thickness in WT and TG plants. FIG. 2G shows sectioning images of WT and TG plant leaves. FIG. 2H shows sectioning images of WT and TG plant roots. FIG. 2I shows the stem diameter in WT and TG plants. Data are presented as means±SE, and error bars represent standard error. Asterisks * indicate a significant difference transgenic and control plants at P<0.01 by Student's t-test test using JMP 9.0.0 software.

FIG. 3A shows tillering and shoot growth of WT and TG plants 90 days after starting as a single tiller. FIG. 3B shows the tiller number of WT and TG plants counted 30 days, 60 days and 90 days after starting as a single tiller. FIG. 3C shows the fresh weight of WT and TG shoots weighed 90 days after starting as a single tiller. FIG. 3D shows the dry weight of WT and TG shoots weighed 90 days after starting as a single tiller. FIG. 3E shows the different root growth of WT and TG plants 90 days after starting as a single tiller. FIG. 3F shows the fresh weight of WT and TG roots weighed 90 days after starting as a single tiller. FIG. 3G shows the dry weight of WT and TG roots weighed 90 days after starting as a single tiller. Statistical analysis was conducted on the control (WT) and transgenic plants. Data are presented as means±SE, and error bars represent standard error. Asterisks * indicate a significant difference transgenic and control plants at P<0.01 by Student t-test using JMP 9.0.0 software.

FIG. 4A shows the fully developed TG and WT plants clonally propagated from individual stolons after being subjected to salt stress (200 mM NaCl). FIG. 4B shows a further view of the salt stressed TG and WT plants. FIG. 4C shows the WT and TG plants after a 12 day recovery from a 12 day treatment with 200 mM NaCl. FIG. 4D shows the relative water content (RWC) of WT and TG plants under salt stress. FIG. 4E shows the electrolyte leakage (EL) from leaf cells of WT and TG plants under normal conditions (0 mM NaCl) and after treatment with two different saline concentrations (200 mM and 300 mM NaCl). FIG. 4F shows the sodium content in WT and TG plants under normal conditions (0 mM NaCl) and after treatment with two different saline concentrations (200 mM and 300 mM NaCl). Data are presented as means±SE, and error bars represent standard error. Asterisks * indicate a significant difference between transgenic and control plants at P<0.01 by Student t-test using JMP 9.0.0 software.

FIG. 5A shows the fully developed WT and TG plants clonally propagated from individual stolons and subjected to dehydrating conditions or drought stress (withholding of water). The photographs were taken at 15 days, 16 days and 20 days after the initiation of drought stress. FIG. 5B shows the relative water content (RWC) of WT and TG plants 20 days after withholding water. FIG. 5C shows the electrolyte leakage (EL) from the leaf cells of WT and TG plants following 20 days of withholding of water. Data are presented as means±SE, and error bars represent standard error. Asterisks * indicate a significant difference between transgenic and control plants at P<0.01 by Student t-test using JMP 9.0.0 software.

FIG. 6A shows tillering and plant growth in WT and TG plants developed from a single tiller of the same size for 30 days, then subjected to 60 days of water stress (limited water supply). FIG. 6B shows the Statistical analysis of tiller numbers in WT and TG plants counted 60 dafter water stress. FIG. 6C shows the length of the longest stem of WT and TG plants. FIG. 6D shows the biomass of WT and TG shoots weighed 60 d after initiation of drought stress. FIG. 6E shows the biomass of WT and TG roots weighed 60 d after initiation of drought stress. Statistical analysis of tiller number, shoot and root biomass was conducted on WT control plants and various transgenic lines. Data are presented as means±SE, and error bars represent standard errors. Asterisks ***indicates a significant difference between transgenic and control plants at P<0.001 by Student's t-test using JMP 9.0.0.

FIG. 7A Leaf RWC of WT and TG plants 20 d after water withholding. FIG. 7B shows leaf EL of WT and TG plants 20 d after water withholding. Statistical analysis of RWC and EL was conducted on WT control plants and the two transgenic lines. Data are presented as means±SE and error bars represent standard error. Asterisk (*) indicates a significant difference between transgenic and control plants at P<0.05 by Student's t-test using JMP 9.0.0.

FIG. 8A shows net photosynthetic rate. FIG. 8B shows stomatal conductance. Data are presented as means±SE and error bars represent standard error. Asterisk (*) indicates a significant difference between transgenic and control plants at P<0.05 by Student's t-test using JMP 9.0.0.

FIG. 9A shows the ratio of leaf surface area/fresh weight ($cm^2/mg$) and FIG. 9B shows the total wax coverage of WT and TG plants. Data are presented as means±SE, and error bars represent standard error. Asterisks * indicate a significant difference between transgenic and control plants at P<0.01 by Student t-test using JMP 9.0.0 software.

FIG. 10A shows semi-quantitative RT-PCR analysis of the expression levels of the 5 putative miR319 target genes in WT and TC: plants. FIG. 10B shows real-time RT-PCR analysis of the expression levels of the four putative miR319 target genes in WT leaves and TG leaves. FIG. 10C shows real-time RT-PCR analysis of the expression levels of the 4 putative miR319 target genes in WT and TG roots. The ΔΔCt method was used for real-time RT-PCR analysis. Three biological replicates and three technical replicates for each biological replicate were used for data analysis followed by student t-test. ACTIN was used as the endogenous control, Error bars indicate ±SE (n=9).

FIG. 12A shows real-time RT-PCR analysis of AsPCF5 gene expression 0 h, 0.5 h and 6 h after exposure to salt stress. FIG. 12B shows real-time RT-PCR analysis of AsPCF6 gene expression 0 h, 0.5 h and 6 h after exposure to salt stress. FIG. 12C shows real-time RT-PCR analysis of AsPCF8 gene expression 0 h, 0.5 h and 6 h after exposure to salt stress. FIG. 12D shows real-time RT-PCR analysis of AsPCF14 gene expression 0 h, 0.5 h and 6 h after exposure to salt stress. The ΔΔCt method was used for real-time RT-PCR analysis. ACTIN was used as the endogenous control. Error bars indicate ±SE (n=3 technical replicates).

FIG. 13A show real-time RT-PCR analysis of AsPCF5 gene expression in plants 0 h, 0.5 h and 6 h after exposure to dehydration stress. FIG. 13B shows real-time RT-PCR analysis of AsPCF6 gene expression in plants 0 h, 0.5 h and 6 h after exposure to dehydration stress. FIG. 13C shows real-time RT-PCR analysis of AsPCF8 gene expression in plants 0 h, 0.5 h and 6 h after exposure to dehydration stress.

FIG. 13D shows real-time RT-PCR analysis of AsPCF14 gene expression level in plants 0 h, 0.5 h and 6 h after exposure to dehydration stress. The ΔΔCt method was used for real-time RT-PCR analsysis. ACTIN was used as the endogenous control. Error bars indicate ±SE (n=3 technical replicates).

DETAILED DESCRIPTION

Figure 1:
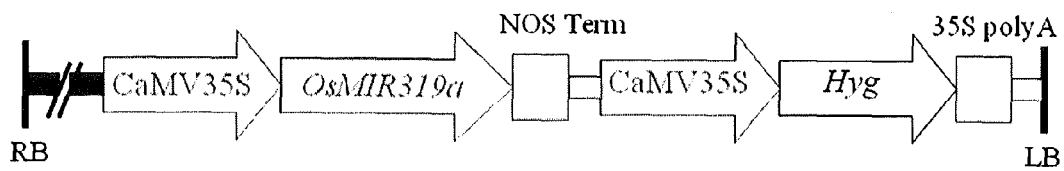
Figure 1:
Figure 1:
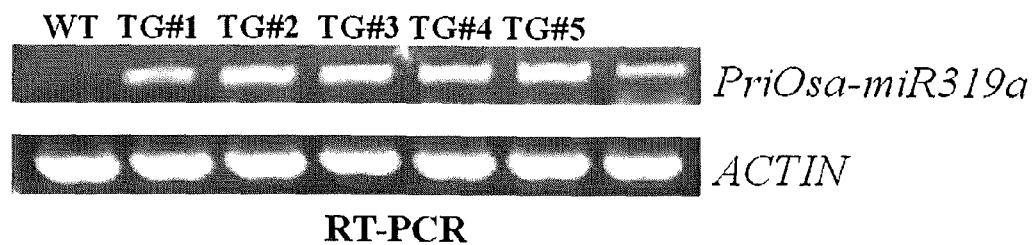
Figure 1:
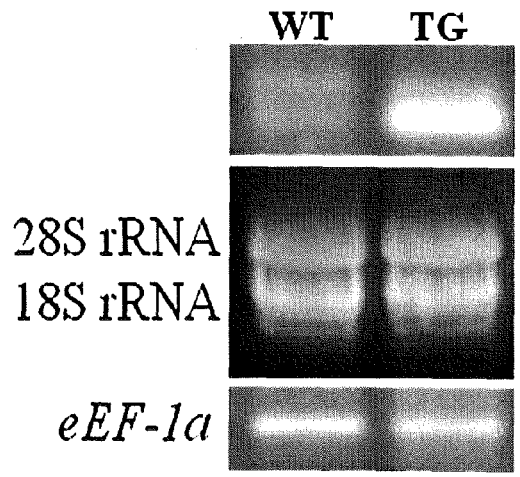

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety The present invention is based in part on the unexpected discovery that the microRNA, miR319, when overexpressed in a transgenic plant results in the plant having increased tolerance to abiotic stress as compared to a plant that is not transformed with miR319 and therefore does not overexpress miR319. The level of expression (e.g., overexpression) of a recombinant nucleic acid molecule comprising miR319 is as compared to the level of expression of an endogenous miR319 in a non-transgenic wild-type plant.

Additionally, it was unexpectedly discovered that a small interfering RNA (e.g., antisense) complementary to a miR319 target gene, PCF5, when expressed in a transgenic plant also results in a plant having increased tolerance to abiotic stress as compared to a plant that does not express said small interfering RNA.

In a first aspect of the invention, a recombinant nucleic acid molecule is provided, the recombinant nucleic acid molecule comprising at least one nucleotide sequence, wherein the at least one nucleotide sequence is; (a) the nucleotide sequence of SEQ ID NO:4; (b) a nucleotide sequence having at least 90% (e.g., 90%, 91%, 92%, 93%, 94%, 95%, 96%, 97%, 98%, 99%, and/or 100%) sequence identity to the nucleotide sequence of (a); (c) a nucleotide sequence which anneals under stringent hybridization conditions to the nucleotide sequence of (a) or (b); (d) a nucleotide sequence that differs from the nucleotide sequences of (a), (b) or (c) above due to the degeneracy of the genetic code; or (e) any combination of the nucleotide sequences of (a)-(d).

In a second aspect of the invention, a transgenic plant having increased tolerance to abiotic stress is provided, the transgenic plant comprising a recombinant nucleic acid molecule, said recombinant nucleic acid molecule comprising, consisting essentially of or consisting of a nucleotide sequence encoding miR319 operatively associated with a promoter, wherein overexpression of the nucleotide sequence confers increased tolerance to abiotic stress as compared to a control plant (e.g., a plant that does not comprise the recombinant nucleic acid molecule comprising a nucleotide sequence encoding miR319 operatively associated with a promoter).

In a third aspect, the present invention provides a transgenic plant having increased tolerance to abiotic stress is provided comprising a recombinant nucleic acid molecule, said recombinant nucleic acid molecule comprising, consisting essentially of, or consisting of: (a) a nucleotide sequence that is antisense to a portion of consecutive nucleotides (e.g., about 21 nucleotides to about 859 nucleotides) of a nucleotide sequence encoding PCF5 and/or (b) a nucleotide sequence that encodes a portion of consecutive nucleotides (e.g., about 21 nucleotides to about 859 nucleotides) of a nucleotide sequence encoding PCF5, which when expressed produces an antisense nucleotide sequence, wherein expression of the antisense nucleotide sequence confers increased tolerance to abiotic stress as compared to a control plant (e.g., a plant that does not comprise said recombinant nucleic acid molecule comprising an antisense nucleotide sequence that is antisense to a portion of consecutive nucleotides of a nucleotide sequence encoding PCF5).

In a fourth aspect, the present invention provides a transgenic plant having increased tolerance to abiotic stress comprising a recombinant nucleic acid molecule, said recombinant nucleic acid molecule comprising, consisting essentially of, or consisting of: (a) a nucleotide sequence that is antisense to a portion of consecutive nucleotides (e.g., about 21 nucleotides to about 859 nucleotides) of the nucleotide sequence of SEQ ID NO:4, and/or (b) a nucleotide sequence that encodes a portion of consecutive nucleotides (e.g., about 21 nucleotides to about 859 nucleotides) of the nucleotide sequence of SEQ ID NO:4, which when expressed produces an antisense nucleotide sequence, wherein expression of the antisense nucleotide sequence confers increased tolerance to abiotic stress as compared to a control plant (e.g., a plant that does not comprise said recombinant nucleic acid molecule).

The present invention further provides a method of producing a transgenic plant having increased tolerance to abiotic stress comprising: a) transforming a plant cell with a recombinant nucleic acid molecule, said recombinant nucleic acid molecule comprising a nucleotide sequence selected from the group consisting of: (i) a nucleotide sequence encoding miR319 operatively associated with a promoter; (ii) a nucleotide sequence that is antisense to a portion of consecutive nucleotides of a nucleotide sequence encoding PCF5, and/or (iii) a nucleotide sequence that encodes a portion of consecutive nucleotides of a nucleotide sequence encoding PCF5, which when expressed produces an antisense nucleotide sequence, to produce a transformed plant cell; and b) regenerating a transgenic plant from the transformed plant cell, thereby producing a transgenic plant having increased tolerance to abiotic stress as compared with a control plant that is not transformed with a recombinant nucleic acid molecule comprising a nucleotide sequence selected from the group consisting of: (i) a nucleotide sequence encoding miR319 operatively associated with a promoter; (ii) a nucleotide sequence that is antisense to a portion of consecutive nucleotides of a nucleotide sequence encoding PCF5, and/or (iii) a nucleotide sequence that encodes a portion of consecutive nucleotides of a nucleotide sequence encoding PCF5.

Any nucleotide sequence encoding a member of the miR319 microRNA family is suitable for the compositions and methods of the invention. Non-limiting examples include the nucleotide sequences encoding miR319 family members identified by the MiRBase database (mirbase.org) as accession numbers MI0000544, MI0000545, MI0005786, MI0001086, MI0001573, MI0001751, MI0001782, MI0001783, MI0001789, MI0001813, MI0001814, MI0001815, MI0001816, MI0002296, MI0002297, MI0002298, MI0002299, MI0002300, MI0002301, MI0002302, MI0002303, MI0002304, MI0003496, MI0003497, MI0003498, MI0003499, MI0005596, MI0005665, MI0006090, MI0006548, MI0006549, MI0006550, MI0006551, MI0007951, MI0009978, MI0010705, MI0010886, MI0012091, MI0013303, MI0013406, MI0013407, MI0013408, MI0013409, MI0014518, MI0014519, MI0014520, MI0014633, MI0016453, MI0016702, MI0017502, MI0018137, MI0018236, and/or MI0005664, and/or the nucleotide sequence of SEQ ID NO:1, and/or any combination thereof, as well as any other nucleotide sequence encoding miR319 now known or later identified.

As would be understood by those of skill in the art, any portion of a nucleotide sequence encoding miR319 that can function as a microRNA is useful with the invention. Accordingly, any portion of a miR319 nucleotide sequence that comprises the stem-loop structure of the miR319 (e.g., a miR319 nucleotide sequences as identified by the accession numbers described herein, the nucleotide sequence of SEQ ID NO:1, the nucleotide sequence of SEQ ID NO:2, and/or the nucleotide sequence of SEQ ID NO:3, and/or any combination thereof) can be used to prepare the recombinant nucleic acid molecules of the invention. In particular embodiments, the nucleotide sequence encoding miR319 can comprise, consist essentially of, or consist of the nucleotide sequence of SEQ ID NO:1, the nucleotide sequence of SEQ ID NO:2 (MiRBase accession no. MI0001098), and/or the nucleotide sequence of SEQ ID NO:3 (MiRBase accession no. MI0001099), and/or any combination thereof.

As known in the art, a processed miRNA transcript can be from about 19 to about 24 nucleotides in length. Therefore, in some embodiments of the invention, the processed miR319 can be about 19-24 nucleotides in length.

Any nucleotide sequence encoding a PCF5 gene is useful with the invention. Such nucleotide sequences encoding PCF5 include those which are homologues to the nucleotide sequence of SEQ ID NO:4. Nonlimiting examples of nucleotide sequences encoding PCF5 include those provided by GenBank® database accession numbers AK241658.1, NM_001048920.1, AP003104.2, AB071805.1, NM_001154053.1, XM_002454900.1, AK376641.1, BT055309.1, BT054865.1, and/or EU971438.1 and/or the nucleotide sequence of SEQ ID NO:4, and/or any combination thereof.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the present invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of this invention has at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 100%) sequence identity to the nucleotide sequences of the present invention (e.g., SEQ ID NO:4).

Further, PCF5 genes of the present invention comprise conserved regions including a TCP domain (basic helix-loop-helix, bHLH) (KDRHSKVCTARGPRDRRVRL-SAHTAIQ FYDVQDRLGYDRPSKAVDWLIKNAK-DAIDKL, SEQ ID NO:9), a Motif 3 domain (GCGEIVEVQGGHIVR, SEQ ID NO:10), a Motif 6 domain (SFLPPSMDSDSIADTIKSFFPV, SEQ ID NO:11)

and a Motif 12 domain (RGTLQSNY, SEQ ID NO:12). See also, SEQ ID NOs:15-18 and Yao et al. (*Journal of Integrative Plant Biology* 49(6):885-897 (2007)).

In some embodiments, the "portion" of consecutive nucleotides of a nucleotide sequence encoding PCF5 comprises, consists essentially of, or consists of any number of consecutive nucleotides of a nucleotide sequence encoding PCF5 (e.g., about 21 to about 860 consecutive nucleotides). The number of nucleotides comprising, consisting essentially of, or consisting of a portion of consecutive nucleotides of a nucleotide sequence encoding PCF5 can be about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, or any range therein, or any combination thereof.

Thus, in some embodiments, the portion of consecutive nucleotides of a nucleotide sequence encoding PCF5 comprises, consists essentially of, or consists of about 21 to about 860 consecutive nucleotides of a nucleotide sequence of PCF5. In other embodiments, the portion of consecutive nucleotides of a nucleotide sequence encoding PCF5 comprises, consists essentially of, or consists of any number of consecutive nucleotides of SEQ ID NO:4. In particular embodiments, the portion of consecutive nucleotides of a nucleotide sequence encoding PCF5 comprises, consists essentially of, or consists of about 21 to about 859 consecutive nucleotides of the nucleotide sequence of SEQ ID NO:4.

It is to be understood that additional nucleotides can be added at the 3' end, the 5' end or both the 3' and 5' ends to facilitate manipulation of the antisense nucleotide sequence but that do not materially affect the basic characteristics or function of the antisense nucleotide sequence molecule in RNA interference (RNAi). Such additional nucleotides can be nucleotides that extend the complementarity of the antisense nucleotide sequence along the target sequence and/or such nucleotides can be nucleotides that facilitate manipulation of the antisense nucleotide sequence or a nucleic acid molecule encoding the antisense nucleotide sequence, as would be known to one of ordinary skill in the art. For example, a TT overhang at the 3' end can be present, which is used to stabilize a siRNA duplex and does not affect the specificity of the siRNA.

To facilitate expression, the recombinant nucleic acid molecules and/or nucleotide sequences of the invention can be operatively associated with one or more promoters. Thus, in some embodiments, the miR319 nucleotide sequence of the invention is operatively associated with a promoter for expression or overexpression of the miR319 nucleotide sequence. In other embodiments, the antisense nucleotide sequence of the invention is under the control of a promoter. In still other embodiments, a promoter is operatively associated with a recombinant nucleic acid molecule which comprises a nucleotide sequence encoding miR319 (e.g., SEQ ID NO:1, SEQ ID NO:2, SEQ ID NO:3, MIRBase database accession numbers MI0000544, MI0000545, MI0005786, MI0001086, MI0001573, MI0001751, MI0001782, MI0001783, MI0001789, MI0001813, MI0001814, MI0001815, MI0001816, MI0002296, MI0002297, MI0002298, MI0002299, MI0002300, MI0002301, MI0002302, MI0002303, MI0002304, MI0003496, MI0003497, MI0003498, MI0003499, MI0005596, MI0005665, MI0006090, MI0006548, MI0006549, MI0006550, MI0006551, MI0007951, MI0009978, MI0010705, MI0010886, MI0012091, MI0013303, MI0013406, MI0013407, MI0013408, MI0013409, MI0014518, MI0014519, MI0014520, MI0014633, MI0016453, MI0016702, MI0017502, MI0018137, MI0018236, MIMAT0001029, and/or MI0005664 and/or any combination thereof) and/or an antisense nucleotide sequence that is antisense to a portion of consecutive nucleotides of a nucleotide sequence encoding PCF5 (e.g, SEQ ID NO:4, GenBank® database accession numbers AK241658.1, NM_001048920.1, AP003104.2, AB071805.1, NM_001154053.1, XM_002454900.1, AK376641.1, BT055309.1, BT054865.1, and/or EU971438.1, and/or any combination thereof). As used herein, the level of overexpression of a recombinant nucleic acid molecule comprising miR319 is as compared to the level of expression of an endogenous miR319 in a non-transgenic wild-type plant.

As used herein, the term "promoter" refers to a region of a nucleotide sequence that provides signals for the expression of a nucleotide sequence operatively associated with the promoter. This may include sequences to which an RNA polymerase binds, but is not limited to such sequences and can include regions to which other regulatory proteins bind, together with regions involved in the control of protein translation and can also include coding sequences. Furthermore, a "promoter" of this invention is a promoter (e.g., a nucleotide sequence) capable of initiating transcription of a nucleic acid molecule in a cell of a plant.

The selection of promoters useable with the present invention can be made among many different types of promoters. Thus, the choice of promoter depends upon several factors, including, but not limited to, cell- or tissue-specific expression, desired expression level, efficiency, inducibility and/or selectability. For example, where expression in a specific tissue or organ is desired in addition to inducibility, a tissue-specific promoter can be used (e.g., a root specific promoter). In contrast, where expression in response to a stimulus is desired a promoter inducible by other stimuli or chemicals can be used. Where continuous expression is desired throughout the cells of a plant, a constitutive promoter can be chosen.

Non-limiting examples of constitutive promoters include cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci. USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter.

Some non-limiting examples of tissue-specific promoters useable with the present invention include those encoding seed storage proteins (e.g., β-conglycinin, cruciferin, napin phaseolin, etc.), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Thus, the promoters associated with these tissue-specific nucleic acids can be used in the present invention.

Additional examples of tissue-specific promoters include, but are not limited to, the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res,* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology*, 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants*, Hollaender ed., Plenum Press 1983; and Poulsen et al. (1986) *Mol. Gen. Genet.* 205:193-200)), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612). Particularly useful for seed-specific expression is the pea vicilin promoter (Czako et al. (1992) *Mol. Gen. Genet.* 235:33-40; as well as U.S. Pat. No. 5,625,136). Other useful promoters for expression in mature leaves are those that are switched on at the onset of senescence, such as the SAG promoter from *Arabidopsis* (Gan et al. (1995) *Science* 270:1986-1988).

In addition, promoters functional in plastids can be used. Non-limiting examples of such promoters include the bacteriophage T3 gene 9 5' UTR and other promoters disclosed in U.S. Pat. No. 7,579,516. Other promoters useful with the present invention include but are not limited to the S-E9 small subunit RuBP carboxylase promoter and the Kunitz trypsin inhibitor gene promoter (Kti3).

In some embodiments, inducible promoters can be used with the present invention. Examples of inducible promoters useable with the present invention include, but are not limited to, tetracycline repressor system promoters, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters. Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421) the benzene sulphonamide-inducible promoters (U.S. Pat. No. 5,364,780) and the glutathione S-transferase promoters. Likewise, one can use any appropriate inducible promoter described in Gatz (1996) *Current Opinion Biotechnol.* 7:168-172 and Gatz (1997) *Annu. Rev. Plant Physiol. Plant Mol. Biol.* 48:89-108.

Thus, any promoter known to those of skill in the art for expression of a nucleotide sequence in a plant can be used with the compositions and methods of the invention. In particular embodiments, the nucleotide sequence encoding miR319 is operatively associated with an actin promoter, a CaMV35S promoter and/or a ubiquitin promoter. In other embodiments, an antisense nucleotide sequence that is antisense to a portion of consecutive nucleotides of a nucleotide sequence encoding PCF5 is operatively associated with a CaMV35S promoter, a ubiquitin promoter and/or an actin promoter.

In further embodiments, the present invention provides transgenic plant cells, transgenic plants, and/or transgenic plant parts comprising a recombinant nucleic acid of the invention (i.e., transgenic plants comprising a recombinant nucleic acid that comprises a nucleotide sequence encoding miR319, a nucleotide sequence that is antisense to a portion of consecutive nucleotides of a nucleotide sequence encoding PCF5 and/or a nucleotide sequence that encodes a portion of consecutive nucleotides of a nucleotide sequence encoding PCF5, which when expressed produces an antisense nucleotide sequence, to produce a transformed plant cell) and methods of producing such plants. The transgenic plant cell, plant and/or plant part of the invention can be stably transformed or transiently transformed.

Additionally, crops comprising a plurality of transgenic plants of the invention are provided. Nonlimiting examples of types of crops comprising a plurality of transgenic plants of the invention include an agricultural field, a golf course, a residential lawn, a road side, an athletic field, and/or a recreational field.

As used herein, "plant" means any plant and thus includes, for example, angiosperms, gymnosperms, bryophytes, ferns and/or fern allies. In some embodiments, the plant cell and/or plant of the invention can be a cell and/or plant of any plant species. Non-limiting examples of plants of the present invention include turf grasses, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bolt choy), cardoni, carrots, napa, okra, onions, celery, parsley, chick peas, parsnips, chicory, peppers, potatoes, cucurbits (e.g., marrow, cucumber, zucchini, squash, pumpkin), radishes, dry bulb onions, rutabaga, eggplant, salsify, escarole, shallots, endive, garlic, spinach, green onions, squash, greens, beet (sugar beet and fodder beet), sweet potatoes, swiss chard, horseradish, tomatoes, turnips, and spices; a fruit and/or vine crop such as apples, apricots, cherries, nectarines, peaches, pears, plums, prunes, cherry, quince, almonds, chestnuts, filberts, pecans, pistachios, walnuts, citrus, blueberries, boysenberries, cranberries, currants, loganberries, raspberries, strawberries, blackberries, grapes, avocados, bananas, kiwi, persimmons, pomegranate, pineapple, tropical fruits, pomes, melon, mango, papaya, and lychee, a field crop plant such as clover, alfalfa, evening primrose, meadow foam, corn/maize (field, sweet, popcorn), hops, jojoba, peanuts, rice, safflower, small grains (barley, oats, rye, wheat, etc.), sorghum, tobacco, kapok, a leguminous plant (beans, lentils, peas, soybeans), an oil plant (rape, mustard, poppy, olive, sunflower, coconut, castor oil plant, cocoa bean, groundnut), *Arabidopsis*, a fibre plant (cotton, flax, hemp, jute), lauraceae (cinnamon, camphor), or a plant such as coffee, sugar cane, tea, and natural rubber plants; and/or a bedding plant such as a flowering plant, a cactus, a succulent and/or an ornamental plant, as well as trees such as forest (broad-leaved trees and evergreens, such as conifers), fruit, ornamental, and nut-bearing trees, as well as shrubs and other nursery stock.

In particular embodiments, a plant cell and/or plant of the invention is a turfgrass. As used herein, turfgrass includes, but is not limited to, *Sporobolus airiodes, Puccinellia distans, Paspalum notatum, Cynodon dactylon, Buchloe dactyloides, Cenchrus ciliaris, Hordeum californicum, Hordeum vulgare, Hordeum brachyantherum, Agrostis capillaries, Agrostis palustris, Agrostis exerata, Briza maxima, Poa annua, Poa ampla, Poa canbyi, Poa compressa, Poa pratensis, Poa scabrella, Poa trivialis, Poa secunda, Andropogon gerardii, Schizachyruim scoparium, Andropogon hallii, Bromus arizonicus, Bromus carinatus, Bromus biebersteinii, Bromus marginatus, Bromus rubens, Bromus inermis, Buchloe dactyloides, Axonopus fussifolius, Eremochloa ophiuroides, Muhlenbergia rigens, Sporobolus cryptandrus, Sporobolus heterolepis, Tripsacum dactyloides, Festuca arizonica, Festuca rubra var. commutate, Festuca rubra var. rubra, Festuca megalura, Festuca longifolia, Festuca idahoensis, Festuca elation, Fescue rubra, Fescue ovina var. ovina, Festuca arundinacea, Alopecurus arundinaceaus, Alopecurus pratensis, Hilaria jamesii, Bouteloua eriopoda, Bouteloua gracilis, Bouteloua curtipendula, Deschampsia caespitosa, Oryzopsis hymenoides, Sorghastrum nutans, Eragrostis trichodes, Eragrostis curvula, Melica californica, Stipa comate, Stipa lepida, Stipa viridula, Stipa cernua, Stipa pulchra, Dactylis glomerata, Koeleria pyramidata, Calamovilfa longifolia, Agrostis alba, Phalaris arundinacea, Stenotaphrum secundatum, Spartina pectinata, Lolium multiflorum, Lolium perenne, Leptochloa dubia, Sitanion hystrix, Panicum virgatum, Aristida purpurea, Phleum pretense, Agropyron spicatum, Agropyron cristatum, Agropyron desertorum, Agropyron intermedium, Agropyron trichophorum, Agropyron trachycaulum, Agropyron riparium, Agropyron elongatum, Agropyron smithii, Elymus glaucus, Elymus Canadensis, Elymus triticoides, Elymus junceus, Zoysia japonica, Zoysia matrella,* and *Zoysia tenuifolia.* In some embodiments, a plant of the present invention is creeping bent grass, *Agrostis palustris*.

As used herein, abiotic stress refers to outside, nonliving factors which can be harmful to plants. Non-limiting examples of abiotic stress include drought, high or excessive salinity, low or cold temperature, freezing, heat or high temperature, high light intensity, ozone and/or any combination thereof. In particular embodiments of the invention, the abiotic stress is drought and/or salinity.

All soils contain some level of salts but it is excessive levels of salts that cause plant stress. Stress due to salinity occurs in "salt affected" soils. These soils are generally divided into two main groups: (1) saline soils which contain sufficient neutral soluble salts to adversely affect the growth of most crops and (2) sodic soils that contain sodium salt capable of alkaline hydrolysis. Salt affects plant growth directly through toxicity but also through reduced water uptake (resulting in water stress) and the reduced ability to take up essential nutrients. Some phenotypic characteristics related to salt stress in plants include smaller leaves and shorter stem internodes (i.e., reduced growth), chlorosis, and the browning and death of leaf edges. Drought stress can result in symptoms similar to those of salt stress and includes symptoms such as wilting, decreased growth, chlorosis and browning and death of leaf edges and premature leaf drop.

Parameters for abiotic stress factors are species specific and even variety specific and therefore vary widely according to the species/variety exposed to the abiotic stress. Thus, while one species may be severely impacted by a salinity level of 4.0 dS m$^{-1}$, another species may not be affected until at least a salinity level of 6.0 dS m$^{-1}$, or even 10.0 dS m$^{-1}$. See, for example, Blaylock, A. D. ("Soil salinity, salt tolerance, and growth potential of horticultural and landscape plants," Univ. Wyoming, Cooperative Extension Service, Bulletin B-988, February 1994) in which different plants are categorized as sensitive, moderately sensitive, moderately tolerant and tolerant depending on the level of soil salinity required to affect plant growth. Thus, for example, the level of salinity that is excessive or high for a sensitive plant species or variety is not the same level of salinity that is excessive or high for a moderately sensitive plant or a tolerant plant. The same is true for other types of abiotic stress such as drought. Thus, a level of drought that can be tolerated by a sensitive plant species/variety is different from the level of drought that can be tolerated by a plant species./ variety that is more drought tolerant. Furthermore, because most crops are exposed to multiple abiotic stresses at one time, the interaction between the stresses affects the response of the plant and its ability to tolerate the specific stresses. Thus, abiotic stress parameters are viewed in terms of particular plant species or varieties and particular abiotic stresses.

"Reduce," "reduced," "reducing" or "reduction" (and other grammatical variations thereof) as used herein means diminished, a decrease in, or a diminution in, for example, plant size, as a response to abiotic stress.

"Increase, "increased, or "increasing" (and other grammatical variations thereof) as used herein means an enhancement or augmentation of, for example, the growth of a plant, as a response to alleviating abiotic stress to which the plant is exposed.

Thus, an "increased tolerance to abiotic stress" as used herein refers to the ability of a plant or part thereof exposed to abiotic stress and transformed with the recombinant nucleic acid molecules of the invention to withstand a given abiotic stress better than a control plant or part thereof (i.e., a plant or part thereof that has been exposed to the same abiotic stress but has not been transformed with the recombinant nucleic acid molecules of the invention). Increased tolerance to abiotic stress can be measured using a variety of parameters including, but not limited to, the size and number of plants or parts thereof, relative water content, electrolyte leakage, stomata conductance, photosynthetic rate, internal $CO_2$ concentration, transpiration rate and/or chlorophyll fluorescence. Thus, in some embodiments of this invention, a transformed plant or part thereof comprising a recombinant nucleic acid molecule of the invention, thereby having increased tolerance to the abiotic stress, would have, for example, greater growth as compared to a plant or part thereof exposed to the same stress but not having been transformed with the said recombinant nucleic acid molecule. An increased tolerance to abiotic stress can be an increase in tolerance of about 10%, 20%, 30%, 40%, 50%, 60%, 70%, 80%, 90%, 100%, or any range therein, as compared to a control plant.

The present invention further provides a product harvested from a transgenic plant and/or part thereof of the invention, wherein the product comprises said recombinant nucleic acid molecule. Nonlimiting examples of a harvested product include a seed, a leaf, a stem, a shoot, a fruit, flower, root, and/or extract. In some embodiments, a processed product produced from the harvested product is provided. Nonlimiting examples of a processed product include a protein, an extract, a medicinal product (e.g., artemicin as an antimalarial agent), a biofuel (e.g., ethanol), and/or a fragrance.

Definitions

As used in the description of the embodiments of the invention and the appended claims, the singular forms "a," "an," and "the" are intended to include the plural forms as well, unless the context clearly indicates otherwise.

As used herein, "and/or" refers to and encompasses any and all possible combinations of one or more of the associated listed items.

The term "about," as used herein when referring to a measurable value such as an amount of a compound, dose, time, temperature, and the like, is meant to encompass variations of 20%, 10%, 5%, 1%, 0.5%, or even 0.1% of the specified amount.

The terms "comprise," "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The terms "nucleotide sequence" "nucleic acid," "nucleic acid molecule," "oligonucleotide" and "polynucleotide" are used interchangeably herein to refer to a heteropolymer of nucleotides and encompass both RNA and DNA, including cDNA, genomic DNA, mRNA, synthetic (e.g., chemically synthesized) DNA or RNA and chimeras of RNA and DNA. The term nucleic acid refers to a chain of nucleotides without regard to length of the chain. A nucleic acid can be double-stranded or single-stranded. Where single-stranded, the nucleic acid can be a sense strand or an antisense strand. A nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. Nucleic acid sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions). In some embodiments, a gene refers to only the coding region. A gene may be "isolated" by which is meant a nucleic acid molecule that is substantially or essentially free from components normally found in association with the nucleic acid molecule in its natural state. Such components include other cellular material, culture medium from recombinant production, and/or various chemicals used in chemically synthesizing the nucleic acid molecule.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," in the context of two nucleic acid molecules, nucleotide sequences or protein sequences, refers to two or more sequences or subsequences that have at least about 70%, least about 75%, at least about 80%, least about 85%, at least about 90%, at least about 95%, at least about 96%, at least about 97%, at least about 98%, or at least about 99% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 50 residues to about 150 residues in length. Thus, in some embodiments of this invention, the substantial identity exists over a region of the sequences that is at least about 50, about 60, about 70, about 80, about 90, about 100, about 110, about 120, about 130, about 140, about 150, or more residues in length. In some particular embodiments, the sequences are substantially identical over at least about 150 residues. In a further embodiment, the sequences are substantially identical over the entire length of the coding regions. Furthermore, in representative embodiments, substantially identical nucleotide or protein sequences perform substantially the same function (e.g., conferring increased resistance to a nematode plant parasite, reducing the growth of a nematode plant parasite, reducing cyst development).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially identical when the two sequences hybridize to each other under stringent conditions. In some representative embodiments, two nucleotide sequences considered to be substantially identical hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the present invention. In one embodiment, a reference nucleotide sequence hybridizes to the "test" nucleotide sequence in 7% sodium dodecyl sulfate (SDS), 0.5 M NaPO$_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M NaPO$_4$, 1 mM EDTA at 50° C. with washing in 1×SSC, 0.1% SDS at 50° C. or in 7% sodium dodecyl sulfate (SDS), 0.5 M NaPO$_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M NaPO$_4$, 1 mM EDTA at 50° C. with washing in 0.1×SSC, 0.1% SDS at 50° C., or in 7% sodium dodecyl sulfate (SDS), 0.5 M NaPO$_4$, 1 mM EDTA at 50° C. with washing in 0.1×SSC, 0.1% SDS at 65° C.

An "isolated" nucleic acid molecule or nucleotide sequence or an "isolated" polypeptide is a nucleic acid molecule, nucleotide sequence or polypeptide that, by the hand of man, exists apart from its native environment and is therefore not a product of nature. An isolated nucleic acid molecule or isolated polypeptide may exist in a purified form or may exist in a non-native environment such as, for example, a recombinant host cell. Thus, for example, with respect to polynucleotides, the term isolated means that it is separated from the chromosome and/or cell in which it naturally occurs. A polynucleotide is also isolated if it is separated from the chromosome and/or cell in which it naturally occurs and is then inserted into a genetic context, a chromosome, a chromosome location, and/or a cell in which it does not naturally occur. The recombinant nucleic acid molecules and nucleotide sequences of the invention can be considered to be "isolated" as defined above.

Thus, an "isolated nucleic acid molecule" or "isolated nucleotide sequence" is a nucleic acid molecule or nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid that is part of a hybrid nucleic acid molecule encoding an additional polypeptide or peptide sequence. An "isolated nucleic acid molecule" or "isolated nucleotide sequence" can also include a nucleotide sequence derived from and inserted into the same natural, original cell type, but which is present in a non-natural state, e.g., present in a different copy number, and/or under the control of different regulatory sequences than that found in the native state of the nucleic acid molecule.

The term "isolated" can further refer to a nucleic acid molecule, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not necessarily mean that the preparation is technically pure (homogeneous), but it is sufficiently pure to provide the polypeptide or nucleic acid in a form in which it can be used for the intended purpose.

In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10.000-fold, 100,000-fold or more enrichment of the nucleic acid (w/w) is achieved as compared with the starting material.

As used herein, "heterologous" refers to a nucleic acid molecule or nucleotide sequence that either originates from another species or is from the same species or organism but is modified from either its original form or the form primarily expressed in the cell. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g. present in a different copy number, and/or under the control of different regulatory sequences than that found in the native state of the nucleic acid molecule.

"Wild-type" nucleotide sequence or amino acid sequence refers to a naturally occurring ("native") or endogenous nucleotide sequence or amino acid sequence. Thus, for example, a "wild-type mRNA" is an mRNA that is naturally occurring in or endogenous to the organism. A "homologous" nucleotide sequence is a nucleotide sequence naturally associated with a host cell into which it is introduced.

By the term "express" or "expression" of a polynucleotide coding sequence, it is meant that the sequence is transcribed, and optionally translated.

"Nucleotide sequence of interest" refers to any nucleotide sequence which, when introduced into a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "nucleotide sequence of interest" may also be one that is transferred to plants for the production of commercially valuable enzymes or metabolites in the plant.

As used herein, the phrases "operably linked," "operatively linked," "operatively associated" or "in operative association" and the like, mean that elements of a nucleic acid construct such as an expression cassette or nucleic acid molecule are configured so as to perform their usual function. Thus, regulatory or control sequences (e.g., promoters) operatively associated with a nucleotide sequence are capable of effecting expression of the nucleotide sequence. For example, a promoter in operative association with a nucleotide sequence encoding miR319 and/or an antisense nucleotide sequence of this invention would be capable of effecting the expression of that miR319 nucleotide sequence and/or antisense nucleotide sequence.

The control sequences need not be contiguous with the nucleotide sequence of interest, as long as they function to direct the expression thereof. Thus, for example, intervening untranslated, yet transcribed, sequences can be present between a promoter and a coding sequence, and the promoter sequence can still be considered "operably linked" to the coding sequence.

As used herein, the terms "transformed" and "transgenic" refer to any plant, plant cell, callus, plant tissue, or plant part that contains all or part of at least one recombinant (e.g., heterologous) polynucleotide. In some embodiments, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, a transgenic plant cell, plant and/or plant part of the invention can be stably transformed or transiently transformed.

The term "plant part," as used herein, includes but is not limited to embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

"Transient transformation" in the context of a polynucleotide means that a polynucleotide is introduced into the cell and does not integrate into the genome of the cell.

As used herein, "stably introducing," "stably introduced," "stable transformation" or "stably transformed" in the context of a polynucleotide introduced into a cell, means that the introduced polynucleotide is stably integrated into the genome of the cell, and thus the cell is stably transformed with the polynucleotide. As such, the integrated polynucleotide is capable of being inherited by the progeny thereof, more particularly, by the progeny of multiple successive generations. "Genome" as used herein includes the nuclear and/or plastid genome, and therefore includes integration of a polynucleotide into, for example, the chloroplast genome. Stable transformation as used herein can also refer to a polynucleotide that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism (e.g., a plant). Stable transformation of a cell can be detected by, for example, a Northern blot hybridization assay of RNA of the cell with nucleic acid sequences which specifically hybridize with a nucleotide sequence of a nucleic acid molecule introduced into a plant or other organism. Stable transformation of a cell can also be detected by, e.g., a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods Transformation can also be detected by direct sequencing and/or hybridization protocols well known in the art.

Transformation

Procedures for transforming plants are well known and routine in the art and are described throughout the literature. Non-limiting examples of methods for transformation of plants include transformation via bacterial-mediated nucleic acid delivery (e.g., via *Agrobacteria*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

Thus, in some particular embodiments, the introducing into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethyleneglycol-mediated transformation, any other electrical, chemical, physical and/or biological mechanism that results in the introduction of nucleic acid into the plant, plant part and/or cell thereof, or a combination thereof.

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hofgen & Willmitzer (1988) *Nucleic Acids Res.* 16:9877).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

Thus, in particular embodiments of the present invention, a plant cell can be transformed by any method known in the art and intact plants can be regenerated from these transformed cells using any of a variety of known techniques. Thus, a plant cell transformed with a nucleic acid molecule of the invention can be regenerated by methods well known in the art to produce a transformed plant or plant part of the invention. Plant regeneration from plant cells, plant tissue culture and/or cultured protoplasts is described, for example, in Evans et al. (Handbook of *Plant Cell Cultures*, Vol. 1, MacMilan Publishing Co. New York (1983)); and Vasil I. R. (ed.) (*Cell Culture and Somatic Cell Genetics of Plants*, Acad, Press, Orlando, Vol. I (1984), and Vol. II (1986)). Methods of selecting for transformed, transgenic plants, plant cells and/or plant tissue culture are routine in the art and can be employed in the methods of the invention provided herein.

Likewise, the genetic properties engineered into the transgenic seeds and plants, plant parts, and/or plant cells of the present invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A nucleotide sequence therefore can be introduced into the plant, plant part and/or plant cell in any number of ways that are well known in the art. The methods of the invention do not depend on a particular method for introducing one or more nucleotide sequences into a plant, only that they gain access to the interior of at least one cell of the plant. Where more than one nucleotide sequence is to be introduced, the respective nucleotide sequences can be assembled as part of a single nucleic acid construct/molecule, or as separate nucleic acid constructs/molecules, and can be located on the same or different nucleic acid constructs/molecules. Accordingly, the nucleotide sequences can be introduced into a cell in a single transformation event, in separate transformation events, or, for example, in plants, as part of a breeding protocol.

In some embodiments of this invention, the introduced nucleic acid molecule may be maintained in the plant cell stably if it is incorporated into a non-chromosomal autonomous replicon or integrated into the plant chromosome(s). Alternatively, the introduced nucleic acid molecule may be present on an extra-chromosomal non-replicating vector and be transiently expressed or transiently active. Whether present in an extra-chromosomal non-replicating vector or a vector that is integrated into a chromosome, the nucleic acid molecule can be present in a plant expression cassette.

Nucleic Acid Constructs

A plant expression cassette or recombinant nucleic acid molecule can contain regulatory or control sequences that drive gene expression in plant cells that are operatively linked so that each sequence can fulfill its function, for example, termination of transcription by polyadenylation signals. Exemplary polyadenylation signals can be those originating from *Agrobacterium tumefaciens* t-DNA such as the gene known as octopine synthase of the Ti-plasmid pTiACH5 (Gielen et al. *EMBO J.* 3:835 (1984)) or functional equivalents thereof, but also all other terminators functionally active in plants are suitable.

Thus, some embodiments of the invention are directed to nucleic acid molecules and/or expression cassettes designed to express the nucleotide sequences and nucleic acid molecules of the invention. Accordingly, in some embodiments, "expression cassette" means a nucleic acid molecule having at least a regulatory or control sequence operatively linked to a nucleotide sequence encoding a miR319 and/or an antisense nucleotide sequence that is antisense to a portion of a nucleotide sequence encoding PCF5. In this manner, for example, plant promoters in operable interaction or associated with the miR319 and/or antisense sequences to be expressed are provided in recombinant nucleic acid molecules and/or expression cassettes for expression in a plant, plant part and/or plant cell, thereby conferring increased tolerance to abiotic stress.

As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. In addition to promoters, discussed above, regulatory sequences include, but are not limited to, enhancers, introns, kozak sequences, translation leader sequences and polyadenylation signal sequences.

A number of non-translated leader sequences derived from viruses are known to enhance gene expression. Specifically, leader sequences from Tobacco Mosaic Virus (TMV, the "w-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711; and Skuzeski et al. (1990) *Plant Mol. Biol.* 15:65-79). Other leader sequences known in the art include, but are not limited to, picornavirus leaders such as an encephalomyocarditis (EMCV) 5' non-coding region leader (Elroy-Stein et al. (1989) *Proc. Natl. Acad. Sci. USA* 86:6126-6130); potyvirus leaders such as a Tobacco Etch Virus (TEV) leader (Allison et al. (1986) *Virology* 154:9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4; Jobling & Gehrke (1987) *Nature* 325:622-625); tobacco mosaic TMV leader (Gallie et al. (1989) *Molecular Biology of RNA* 237-256); and MCMV leader (Lommel et al. (1991) *Virology* 81:382-385). See also, Della-Cioppa et al. (1987) *Plant Physiol.* 84:965-968.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operatively linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and the pea rbcs E9 terminator. These can be used in both monocotyledons and dicotyledons. In addition, a coding sequence's native transcription terminator can be used.

A signal sequence can be operatively linked to a nucleic acid molecule of the present invention to direct the nucleic acid molecule into a cellular compartment. In this manner, the expression cassette will comprise a nucleic acid molecule of the present invention operatively linked to a nucleotide sequence for the signal sequence. The signal sequence may be operatively linked at the N- or C-terminus of the nucleic acid molecule.

The expression cassette also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hyg (hygromycin phosphotransferase) that confers resistance to hygromycin.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts*, 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of this invention.

The present invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1. Construction of Plant Expression Vectors

The full length cDNA of Osmir319a was amplified using the gene specific primers Osmir319aFL_XbaF: 5'-TCTAGAAGAGCCATGGCATTGCT-3' (SEQ ID NO:5) and Osmir319aFL_SalR: 5'-GTCGACGCAAAAGAAA-AATACTACATGATTG-3' (SEQ ID NO:6). The amplified cDNA was then double digested with XbaI and SalI. The amplified cDNA digested with XbaI and SalI was cloned to the binary vector pZH01 (Han et al., *Plant Mol. Biol.* 52:957-966 (2003)) thus obtaining the "p35S-Osmir319aFL/p35S-hyg" construct. The construct contains the 35S promoter driving the full length cDNA of Osmir319aFL and a $^{35}$S promoter driving the nucleotide sequence encoding hygromycin resistance (hyg; selectable marker). The construct was transferred into *Agrobacterium tumefaciens* strain LBA4404 by electroporation for subsequent plant transformation.

Example 2. Plant Material, Growth Conditions and Transformation

A commercial cultivar of creeping bentgrass (*A. stoloniferal* L.) cv. Penn A-4 was used for transformation. Transgenic creeping bentgrass overexpressing Osmir319a were produced using *Agrobacterium*-mediated transformation of embryogenic callus initiated from mature seeds essentially as previously described (Luo et al. *Plant Cell Reports* 22:645-652 (2004)). The regenerated plants were transferred to commercial potting mixture soil (Fafard 3-B Mix, Fafard Inc., Anderson, S.C., USA) or pure silica sand, and maintained in the greenhouse under a 16 h photoperiod with supplemental lighting (27° C. in the light, 25° C. in the dark).

Example 3. Plant DNA Isolation and Southern Blot Analysis

Plant genomic DNA was extracted as previously described using the cetyltrimethyl ammonium bromide (CTAB) method (Luo et al. *Mol. Breed.*, 16, 185-188 (2005)). Twenty micrograms of the genomic DNA was digested with BamHI (which cuts once within the T-DNA region) according to supplier's instruction (New England Biolabs, Beverly, Mass., USA). The digested DNA was then separated by electrophoresis using 0.8% agarose gels, after which the DNA was transferred onto nylon membranes (GE Healthcare Bio-Sciences Corp., Piscataway, N.J., USA), and probed with a 32P-labelled DNA probe of a hyg (i.e., hph) gene fragment. Hybridization was carried out in modified Church and Gilbert buffer at 65° C. following the standard protocol (Sambrook Molecular Cloning: A Laboratory Manual. *Cold Spring Harbor Laboratory*, Cold Spring Harbor, N.Y., 267, 9289-9293 (1989)). Hybridizing fragments were detected by exposure of the membrane on a phosphor screen at RT overnight and scanning on a Typhoon 9400 phosphorimager. The hybridization signals were indication of transgene copy number.

Example 4. Stem-Loop Reverse Transcription and Small RNA Northern

Stem-loop reverse transcription was preformed following the established protocol (Varkonyi-Gasic et al. *Plant Methods*, 3: 12 (2007)). Small RNA northern was performed following protocols known in the art. (Thiebaut et al., Plant Cell Environ., Oct. 23, 2011; doi: 10.1111/j.1365-3040.2011.02430.x)

Example 5. Propagation, Maintenance and Characterization of the Transformed Plants To produce sufficient materials for use in evaluating the plant response to salt and drought stress, wild-type and transgenic plants were clonally propagated in small containers (CONE-TAINERS™; 40×20.3, Dillen Products, Middlefield, Ohio, USA) (five individual stolons per small container) and big pots (15×10.5 cm, Dillen Products, Middlefield, Ohio, USA) (50 individual stolons per pot) using pure silica sand.

The plants were grown in the greenhouse for four weeks. They were then moved to a growth room and put under a 14 h photoperiod for 10 weeks. The grasses were mowed weekly to achieve uniform growth. Illumination condition in the growth room was 350-450 µmol m-2s-1 photosynthetically active radiation at canopy height provided by AgroSun Gold 1000 W sodium/halide lamps (Maryland Hydroponics, laurel, MD, USA). Temperature and humidity were maintained at 25° C. and 30% in the daytime and 17° C. and 60% at night. The plants were watered and fertilized every other day with 200 ppm of 20-10-20 PEAT-LITE SPECIAL® (The Scotts Company, Marysville, Ohio, USA).

Salinity.

For plants grown in CONE-TAINERS™, the salinity treatment was conducted by injecting into the containers 10 ml 200 ppm 20-10-20 fertilizer supplemented with 200 mM or 300 mM NaCl twice every day. For plants grown in the big pots, the salinity treatment was conducted by immersing entire pots in 1 L 0 mM (control), 200 mM and 300 mM NaCl, respectively overnight every other day and on the intervening day for 1 h. The grass shoots were harvested 12 days later, and used for measuring mineral contents and other analyses. To investigate plant recovery from salt stress, the plants were watered with 200 ppm 20-10-20 fertilizer only for an additional 12 days. Photographs were used to document recovery.

Drought.

For drought treatment, water was withheld from both the wild-type and transgenic plants for 20 days. The grass shoots were harvested following the 20 days of drought treatment and used for physiological analyses.

Example 6. Leaf Analysis

Measurement of Mineral Content in the Leaves.

After salt treatment, plant leaf samples were collected and their sodium content determined. All shoots of the creeping bentgrass plants were rinsed in Millipore (Billerica, Mass., USA) water for 30 s. The shoots were dried for 48 h at 80° C., and the dry weights (DWs) measured. Sodium content was determined using Spectro ARCOS ICP (Spectro, Mahwah, N.J., USA) following the protocols of Haynes R. J. (*Commun. Soil Sci. Plant Anal.* 11:459-467 (1980)) and Plank, C.O. (Southern CooperativeSeries Bulletin 368:9 (1992)).

Measurement of Leaf Relative Water Content (RWC).

The leaves from both the wild-type and transgenic plants were harvested (drought and salt treated and respective controls) and immediately weighed to determine fresh weight (FW). They were then immersed in Millipore water at 4° C. for 16 h, and then weighed again to determine turgid weight (TW). After measuring the TW, the leaves were dried at 80° C. for 24 h, and weighed to determine dry weight (DW). Leaf RWC was calculated using the following formula: RWC=[(FW−DW)/(TW−DW)]×100% (Li et al. *Plant Cell Environ.* 33, 272-289 (2010)).

Measurement of Leaf Electrolyte Leakage (EL).

Leaf EL was measured to evaluate cell membrane integrity. For EL measurement, the methods of Li et al. were followed (*Plant Cell Environ.* 33, 272-289 (2010)). Fresh leaf samples (0.2-0.5 g) were incubated in 20 ml Millipore water at 4° C. for 16 h. The initial conductance of the incubation solution ($C_i$) was measured using a conductance meter (AB30, Fisher Scientific, Suwanee, Ga., USA) to estimate the amount of ions released from cells under different conditions (e.g., salinity and drought treatments). The leaf tissue was then autoclaved for 30 min, in the incubation solution. After cooling down on a shaker with 24 h incubation, the conductance of the incubation solution was determined again ($C_{max}$). Relative percent EL was calculated as $(C_i/C_{max})\times100\%$. This analysis reflects the percentage of ions released from the plant cells, thus providing the difference in the stability of the cell membranes of wild-type and transgenic plants under drought and salinity conditions.

Leaf Sections and Microscopic Analysis.

The top third of fully expanded leaves was collected and fixed in formalin-acetic acid-alcohol (FAA). The samples were dehydrated using graded ethanol, and then infiltrated in catalyzed resin (1.25 g of benzoyl peroxide/100 ml of immunobed monomer A). The samples were then embedded, polymerized at room temperature and placed in a dessicator under vacuum until ready to block. The prepared samples were sectioned and stained with 1% toluidine blue and photographed using a microscope (MEIJI EM-5) connected with a 35 mm SLR camera body (Canon).

Cuticular Wax Analysis.

Leaf wax composition measurement was done according to Kosma et al. (*Plant Physiology* 151:1918 (2009)). Leaves were submerged in hexane for 45 s. Wax extracts were evaporated under N2 gas and derivatized by heating at 100° C. for 15 min in N,O-bis(trimethylsily)trifluoroacetamide (BSTFA; Supelco). Silylated samples were analyzed by gas chromatography (GC) with a Hewlett-Packard 5890 series II gas chromatography equipped with a flame ionization detector and a 12-m, 0.2-mm HP-1 capillary column with helium as the carrier gas. The oven temperature was programmed with an initial temperature of 80° C. and increased at a rate of 15° C. per minute to 260° C., at which point the temperature remained unchanged for 10 min. The temperature was then increased at 5° C. per minute to 320° C., at which point the temperature was held at 320° C. for 24 min. The injector and detector temperatures were set at 320° C. Quantification was based on flame ionization detector (FID) peak areas relative to the internal standard tetrococine.

The method of Bondada et al. (*Environ. Exp. Bot* 36: 61-65, 67-69 (1996)) was used to determine the total cuticle wax content of turfgrass leaves. Leaves were immersed and agitated for 45 s in a series of preweighed test tubes containing hexane. The hexane was then evaporated off using a nitrogen evaporator and the test tubes were weighed. The wax content was calculated by subtracting the initial weight of the test tube from its final weight. The total amount of cuticular wax was expressed per unit of leaf surface area (ug dm-2). Leaf area was determined using ImageJ software from the NIH (rsb.info.nih.gov/ij/) and digital images of flattened leaves.

Statistical Analysis.

The Student's t-test was used to analyze all of the data comparing the results from the wild-type and the transgenic plants under normal and stress conditions. A p value of <0.01 or <0.05 was considered to be statistically significant.

Example 7. Production and Molecular Characterization of Transgenic Creeping Bentgrass Plants Overexpressing Os_mirR319 Gene The pre-mir319a sequence was obtained from the miR-Base (version 13.0c, microma.sanger.ac.uk/sequences/). This sequence was then used to search the rice full length cDNA database (Kome, cdna01.dna.affrc.go.jp/cDNA/), one FL-cDNA clone AK064418 corresponding to pri-miR319a was identified. In rice genomics, AK064418 corresponds to Os01g0659400, which encodes the rice mir319a gene. Os01g0659400 was renamed Osmir319a and employed for overexpression in creeping bent grass.

The rice mir319a gene was overexpressed in transgenic creeping bentgrass plants to observe its impact on turfgrass.

To generate transgenic plants expressing Osmir31a, one chimeric DNA construct was prepared containing the sequence of Osmir319aST, including the stem-loop structure (FIG. 1A). A rice actin promoter was used to drive the Osmir319a expression and a nucleotide sequence that confers hygromycin-resistance driven by the CaMV 35 S promoter was included as a selectable marker for plant transformation (FIG. 1A), p35S-hyg/actin-osmiR319a.

Using Agrobacterium-mediated transformation, the chimeric gene construct, p35S-hyg/actin-Osmir319aST, was introduced into embryogenic callus derived from mature seeds of a creeping bentgrass (A. stolonifera L.) cultivar, Penn A-4.

Hygromycin selection was used to identify transformants. A total 15 independent TO transgenic lines were produced. PCR amplification of genomic DNA from transgenic plants confirmed the presence of transgenes (FIG. 1B).

RT-PCR analysis demonstrated that the transgenic turfgrass was overexpressing the rice primary miR319a transcript (FIG. 1C). Results from the stem-loop RT-PCR detected the mature osmiR319a, indicating that the primary osmiR319a was properly processed in transgenic creeping bentgrass (FIG. 1D).

Example 8. Morphological Characterization of Transgenic Creeping Bentgrass

Figure 2:
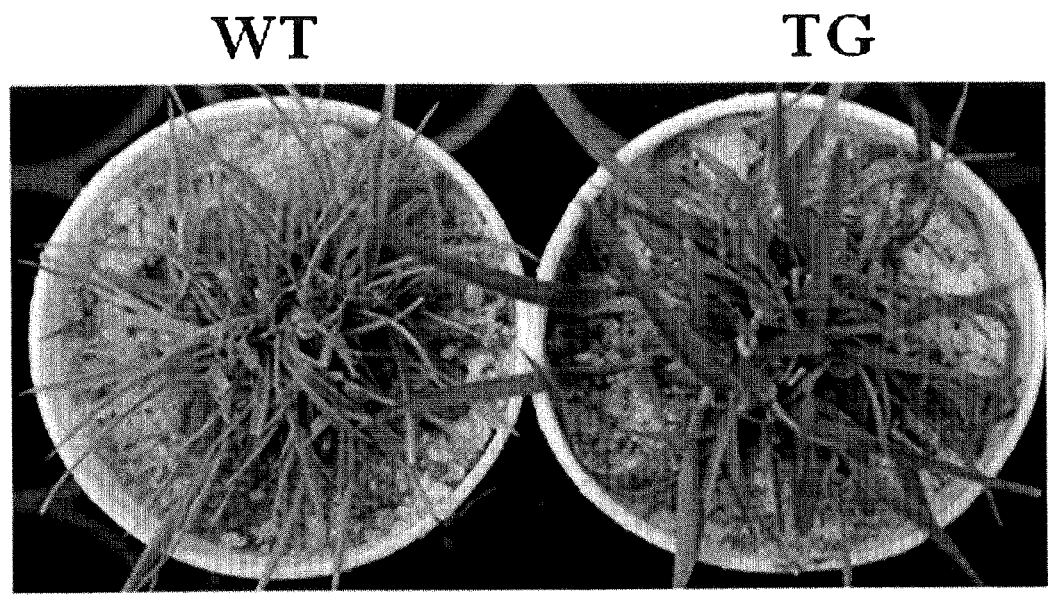
Figure 2:
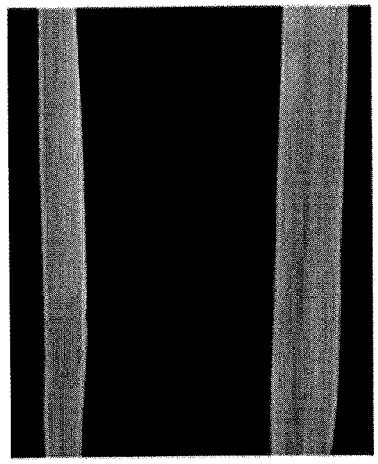
Figure 2:
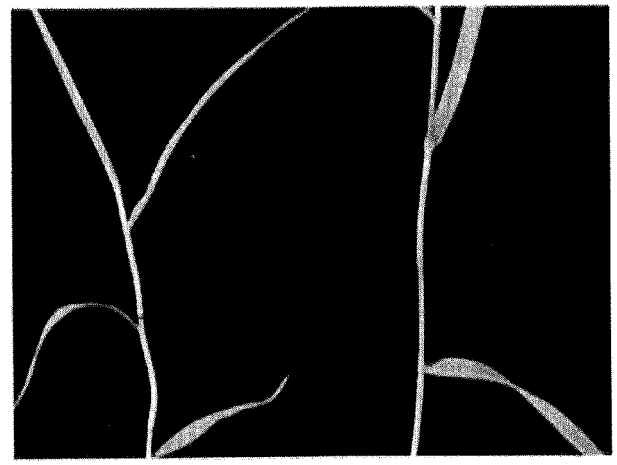
Figure 2:
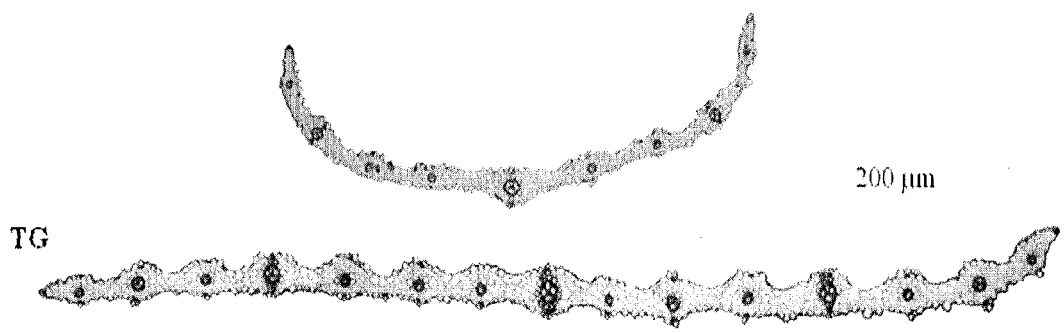
Figure 2:
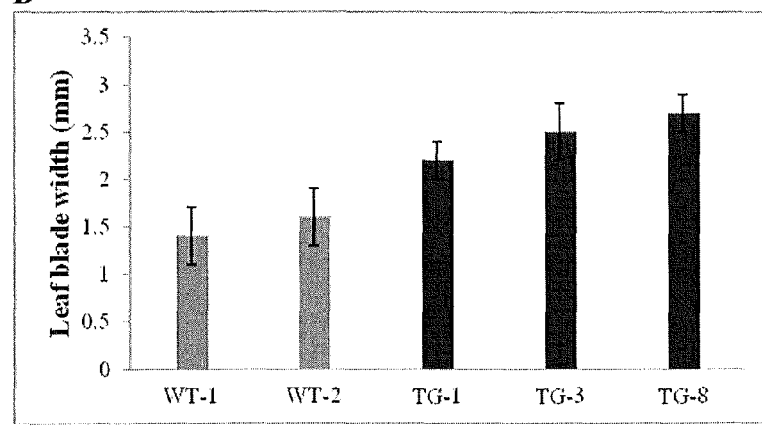
Figure 2:
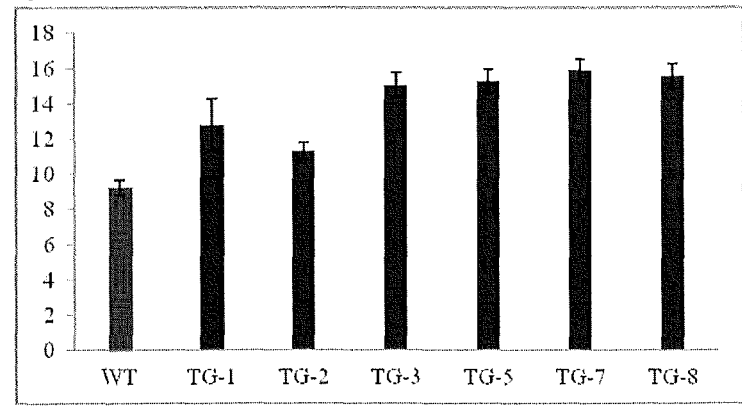
Figure 2:
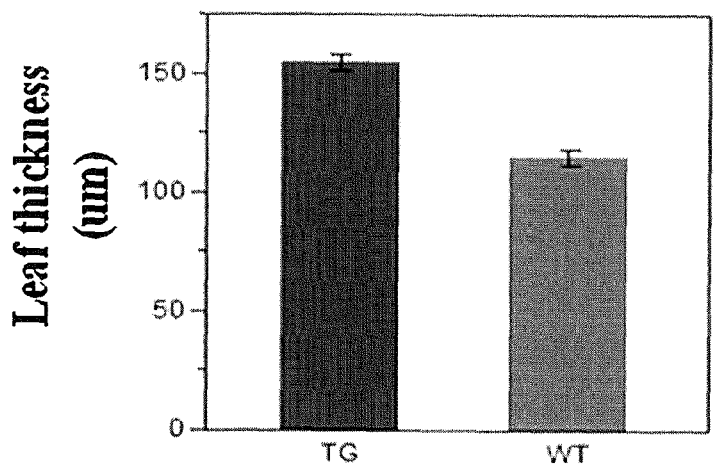
Figure 2:
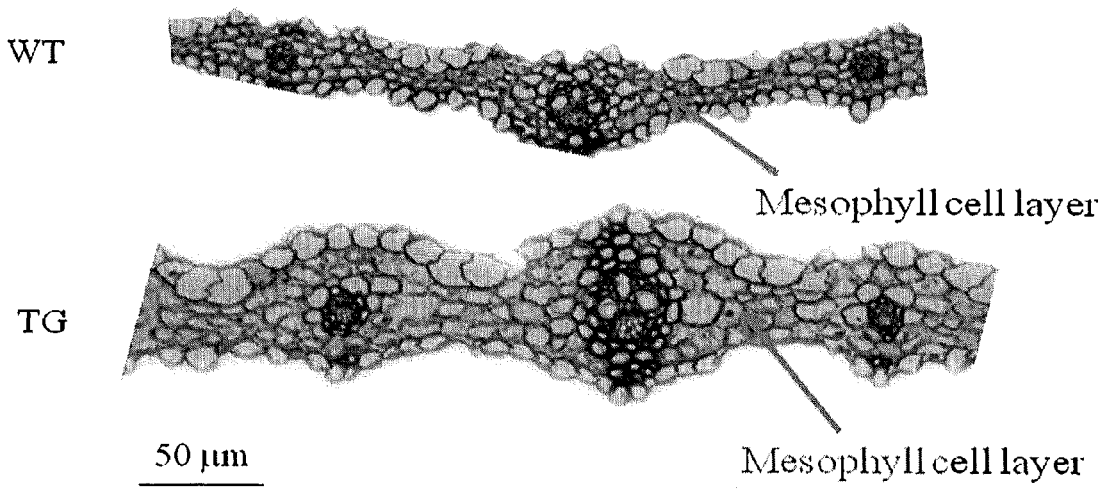
Figure 2I:
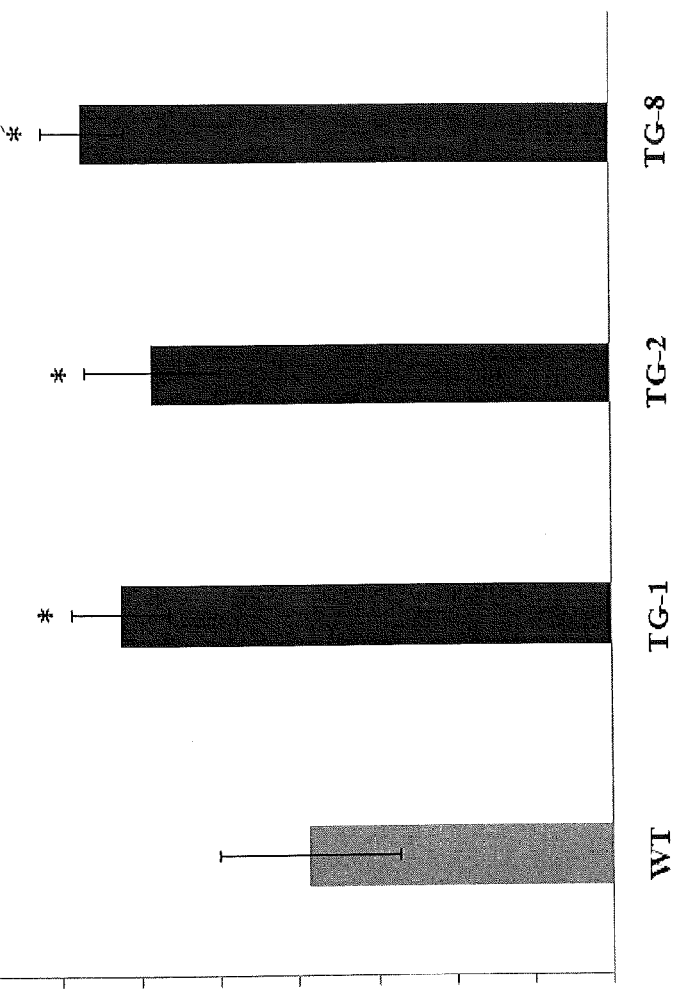
Figure 2H:
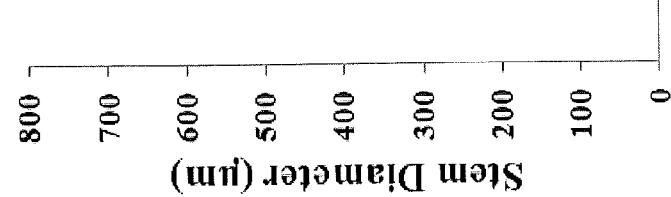
Figure 2H:
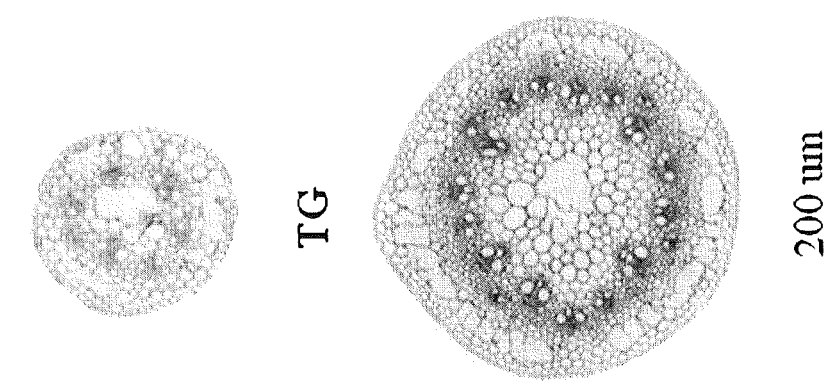

The transgenic creeping bentgrass plants overexpressing OsmiR319a exhibited wider leaves and coarser stems when compared with wild-type plants (FIGS. 2A, 2B). The microscopic and statistical analysis of leaf width and vein number supports this observation. A microscopic view of the leaves shows that the leaves of transgenic plants are wider than those of WT (FIG. 2C). Both the leaf blade width and the total vein number in the leaves of the transgenic plants are significantly larger than those of wild-type (FIGS. 2D, 2E). The leaves of transgenic plants have increased leaf thickness (FIG. 2F) and increased thickness of mesophyll cell layers (FIG. 2G) compared to that of the wild-type control. In stems, overexpression of OsmiR319a leads to an increased stem diameter in transgenic plants as shown in FIGS. 2H and 2I.

Figure 3:
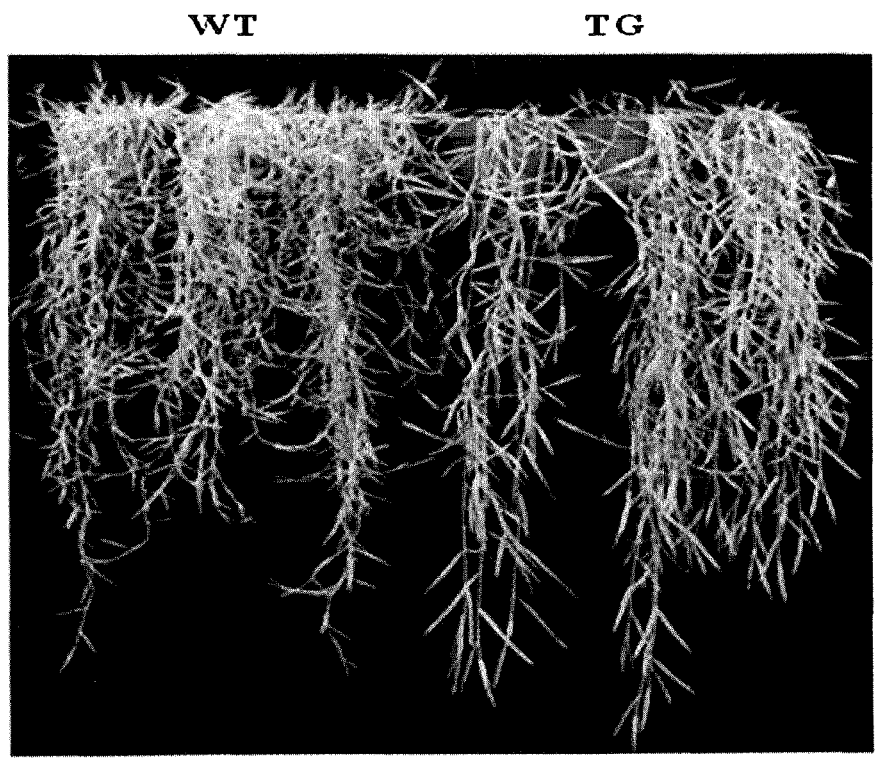
FIGS. 3A-3G show tillering and growth development of WT and TG plants starting from a single tiller.
Figure 3:
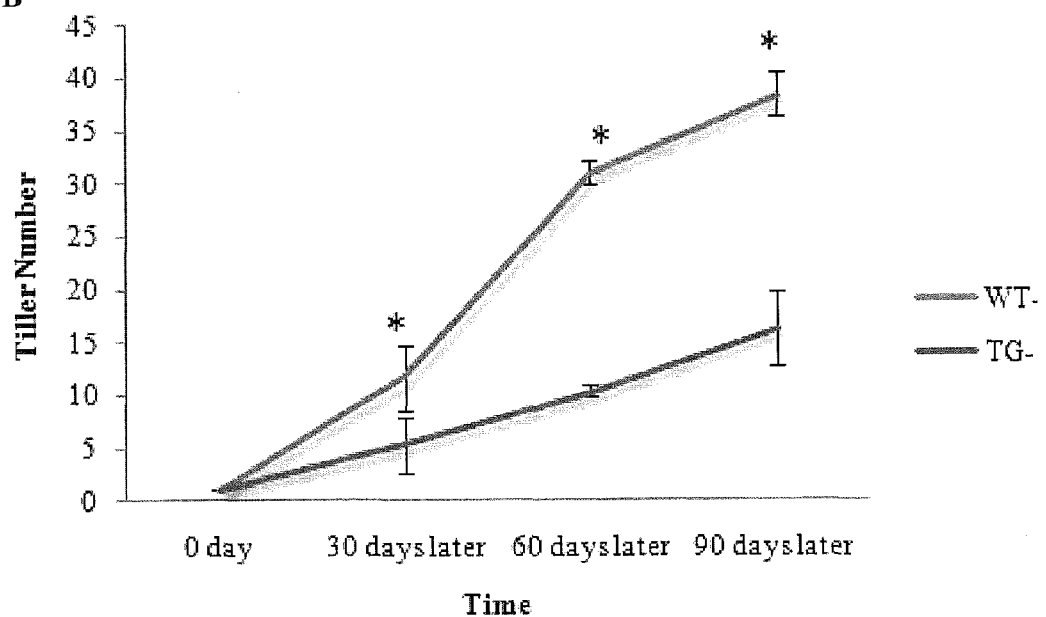
Figure 3:
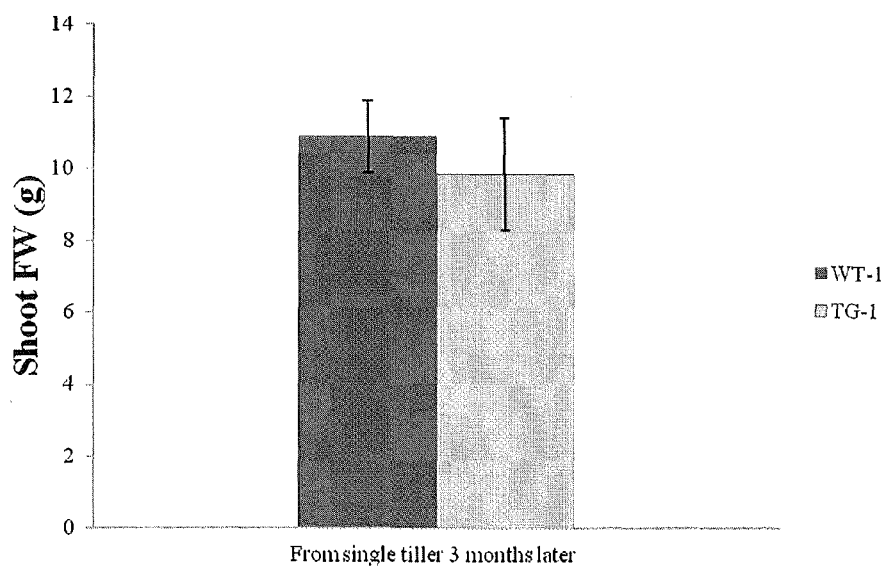
Figure 3:
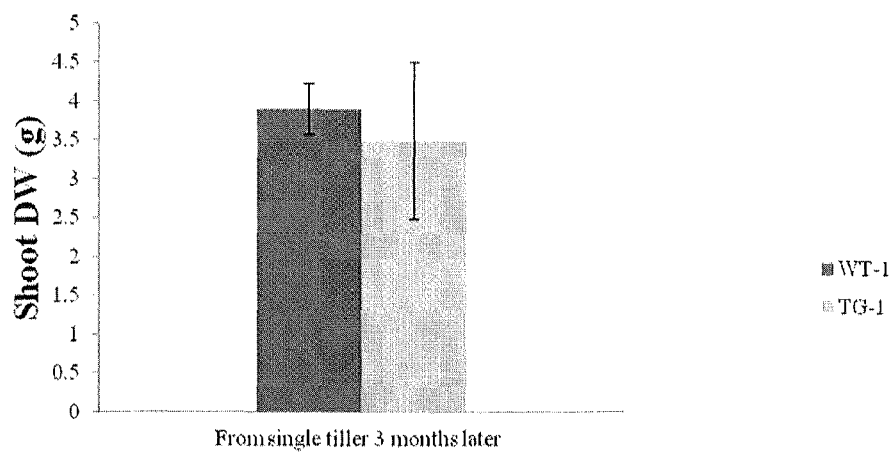
Figure 3:
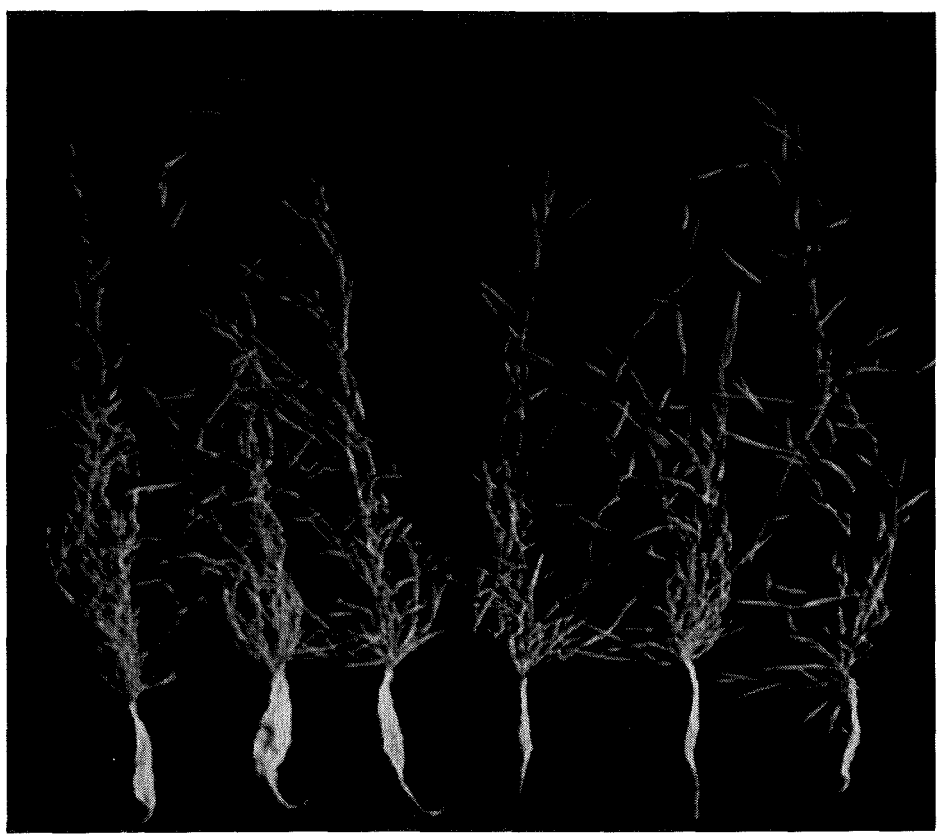
Figure 3:
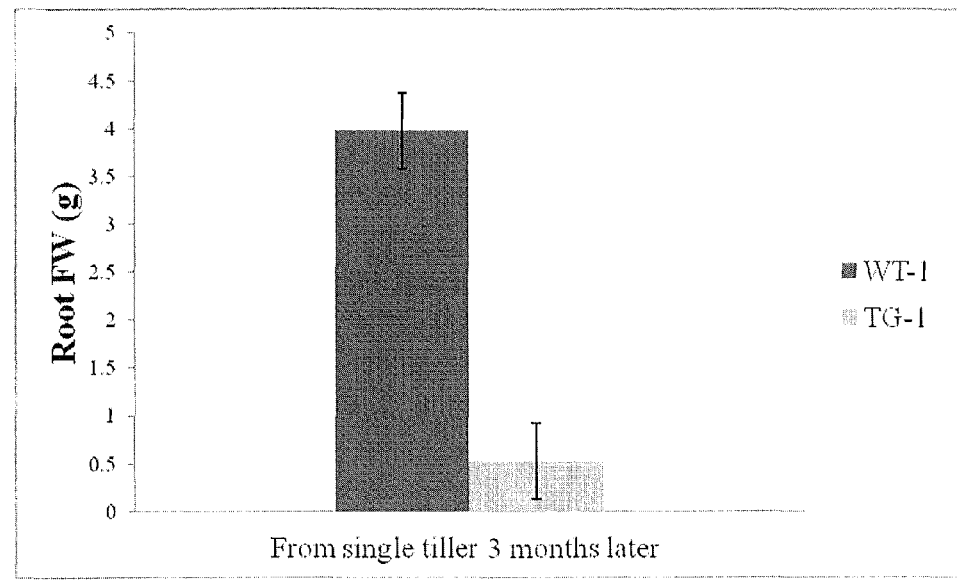
Figure 3:
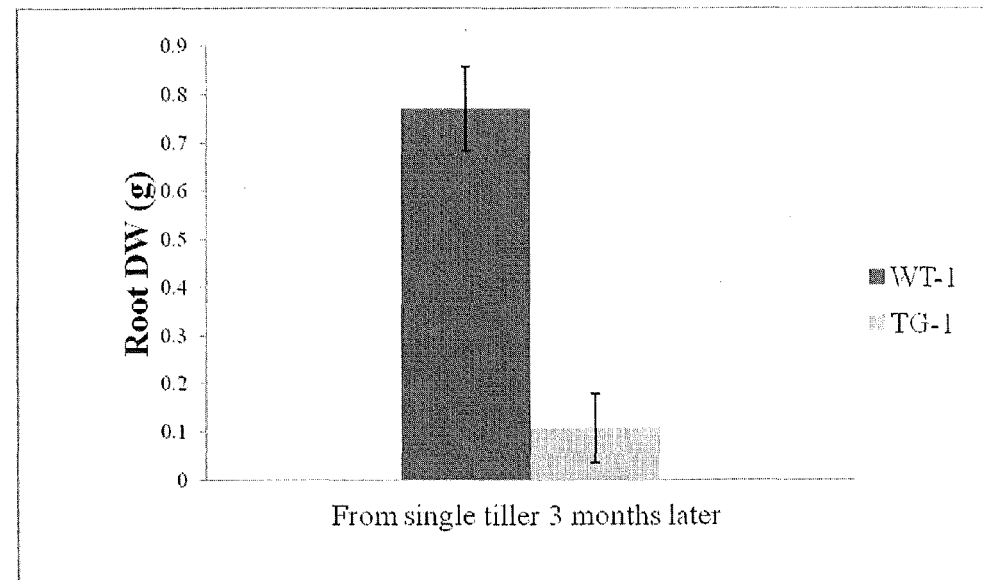

Transgenic and wild-type plants were also developed starting from a single tiller. The tiller number was counted at different time points and the fresh weight and dry weight of wild-type and transgenic plant shoots was measured. Overexpression of Osmir319a resulted in reduced tillering (FIGS. 3A, 3B) and lower root biomass (FIGS. 3E-3G). However, no difference was observed between the fresh weight and dry weight of the WT and TG plant shoots (FIGS. 3C, 3D).

Figure 4:
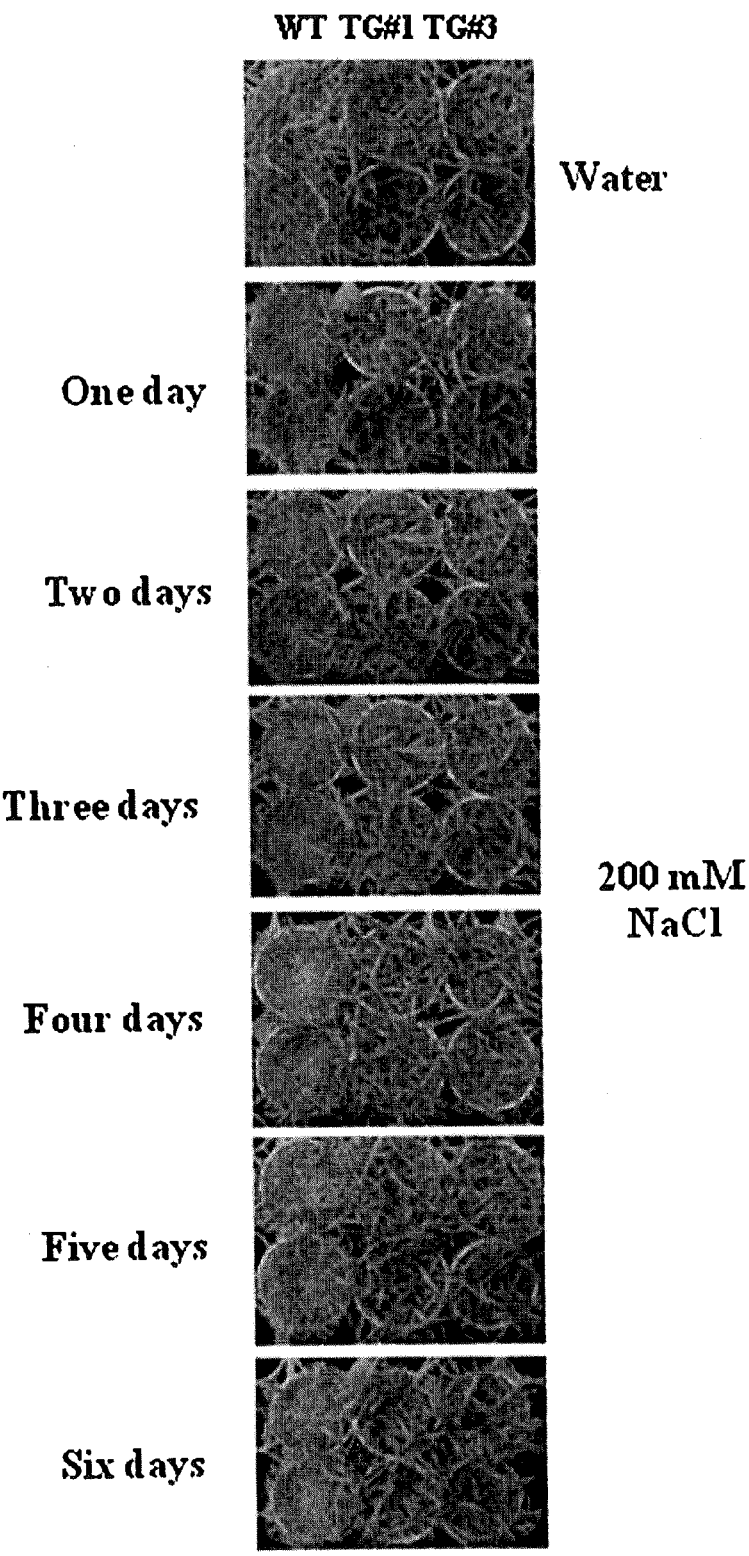
FIG. 4A-4F shows the response of WT and TG plants to salt stress.
Figure 4:
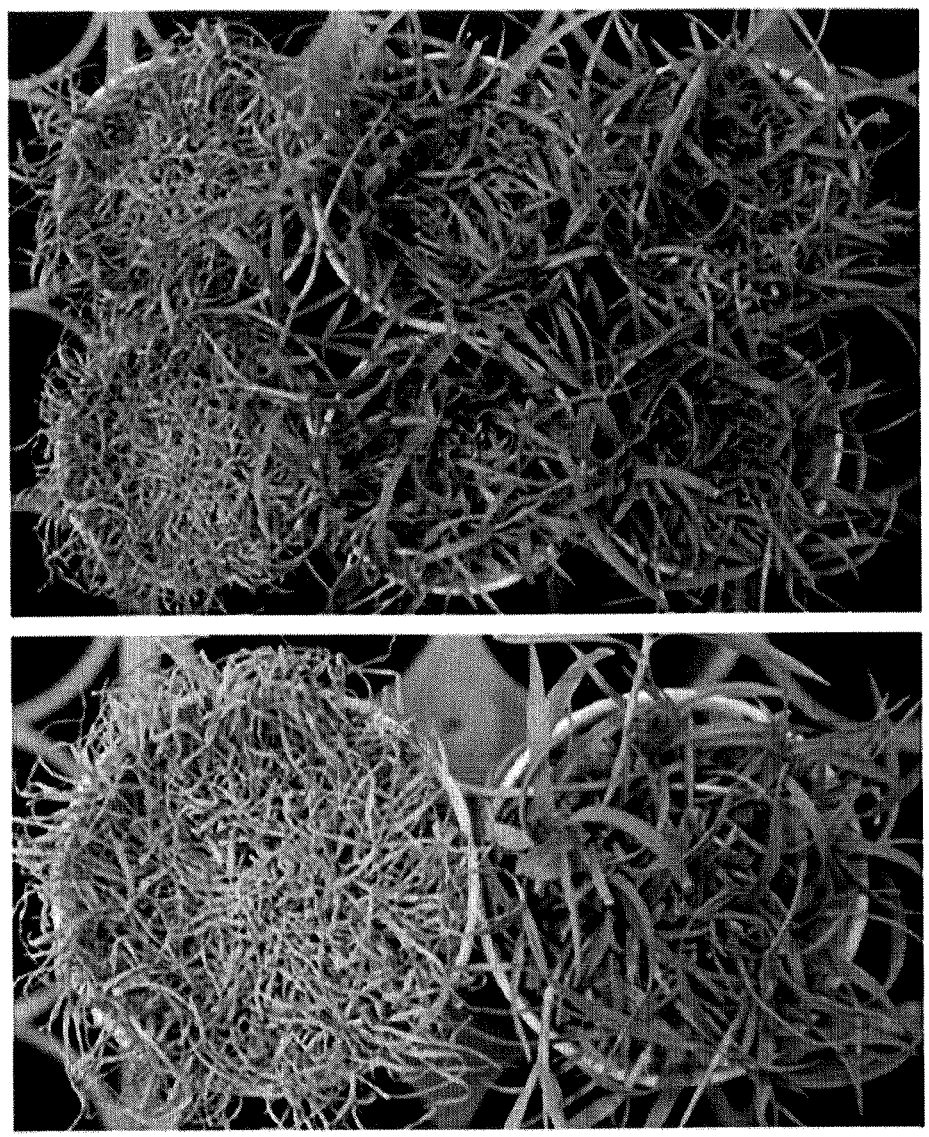

Example 9. Over-Expression of Os_miR319 Results in Enhanced Salt Tolerance in TG Creeping Bentgrass To test the effects of saline conditions on WT and TG plants, both were treated with 200 mM NaCl. Six days after beginning the treatment, the WT plants were observed to be completely damaged (e.g., yellow, complete loss of turgor, all withered), while the TG plants were much less affected (e.g., showed slight symptoms but still turgid and green) (FIGS. 4A and 4B).

Figure 4C:
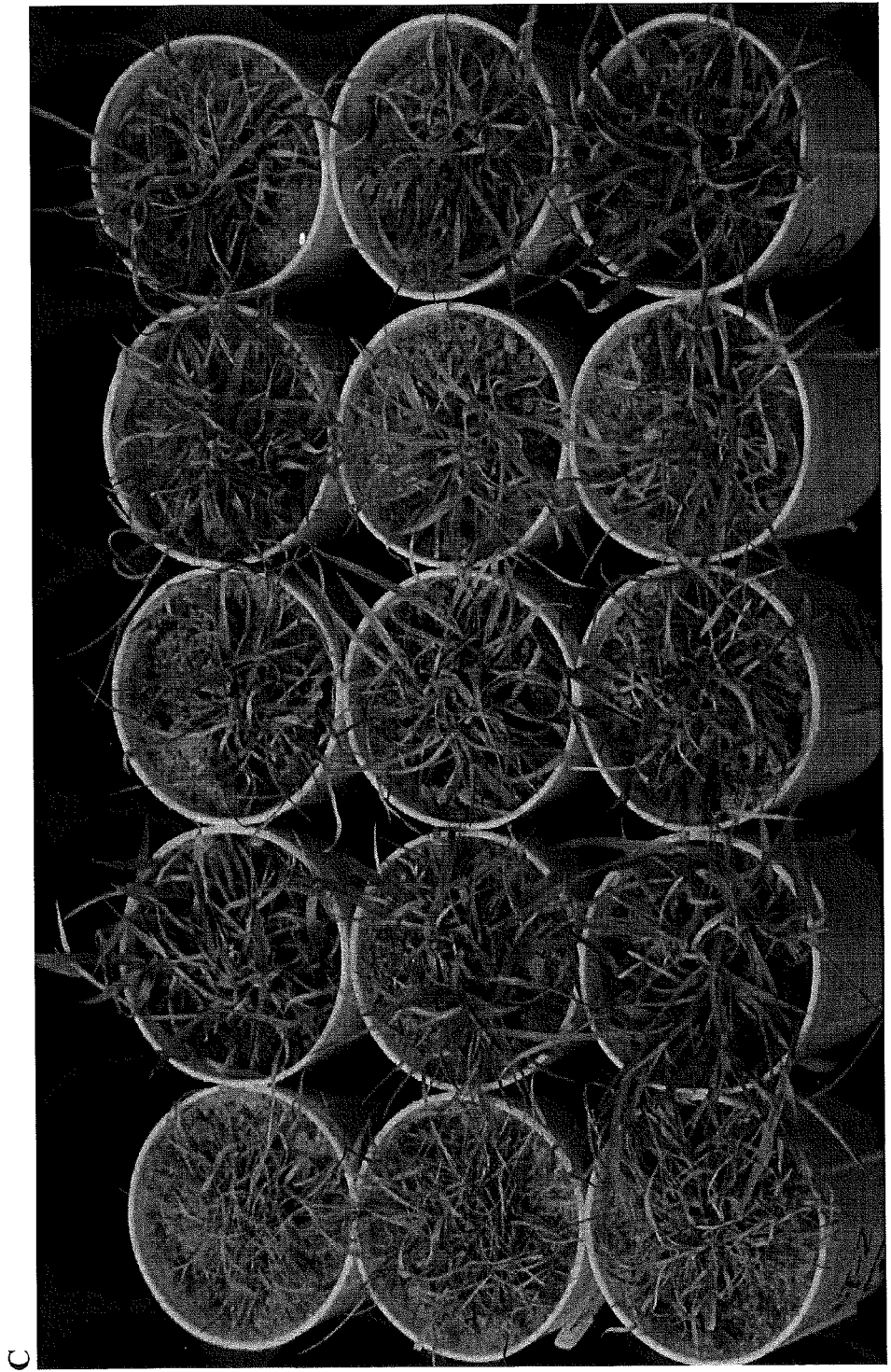
Figure 4:
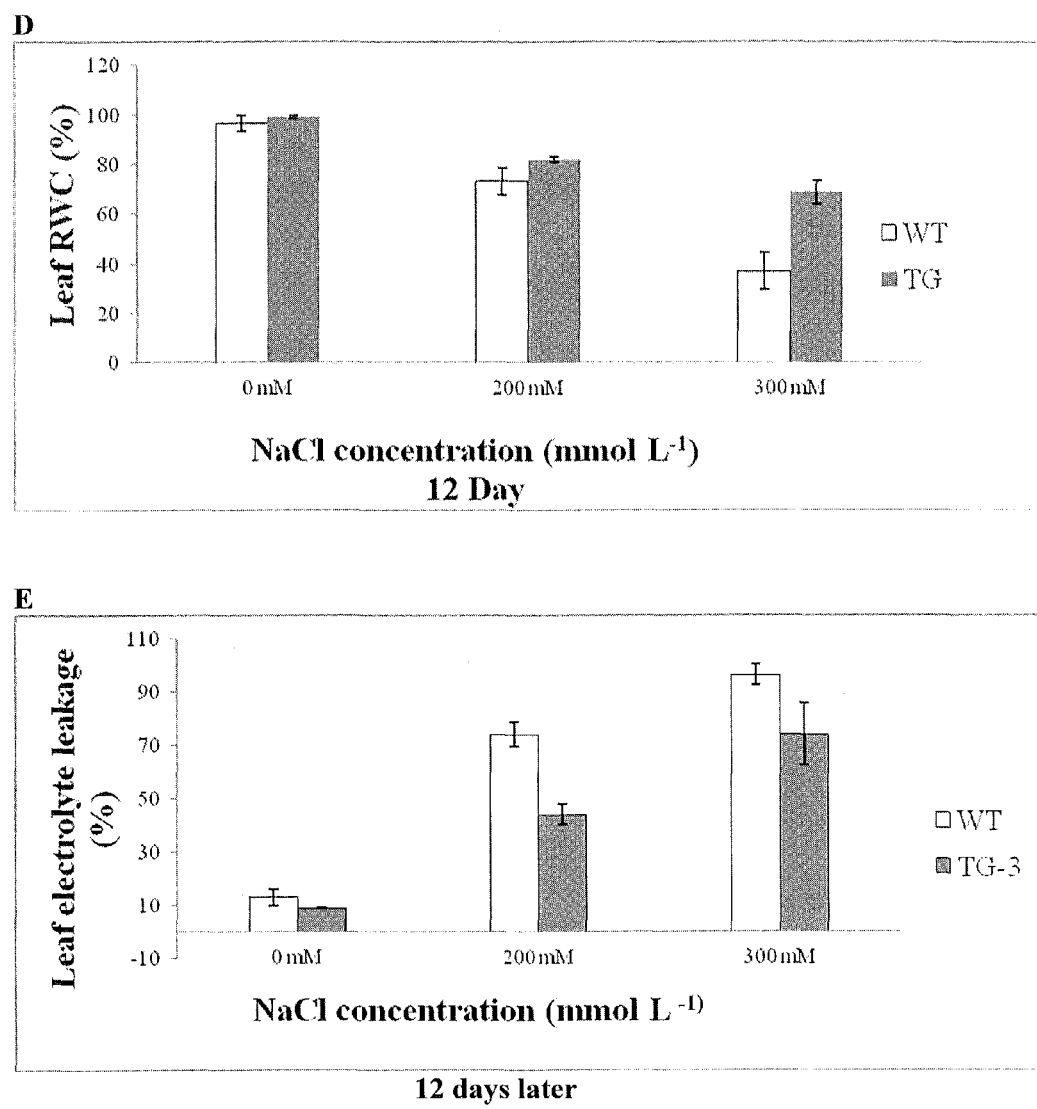
Figure 4:
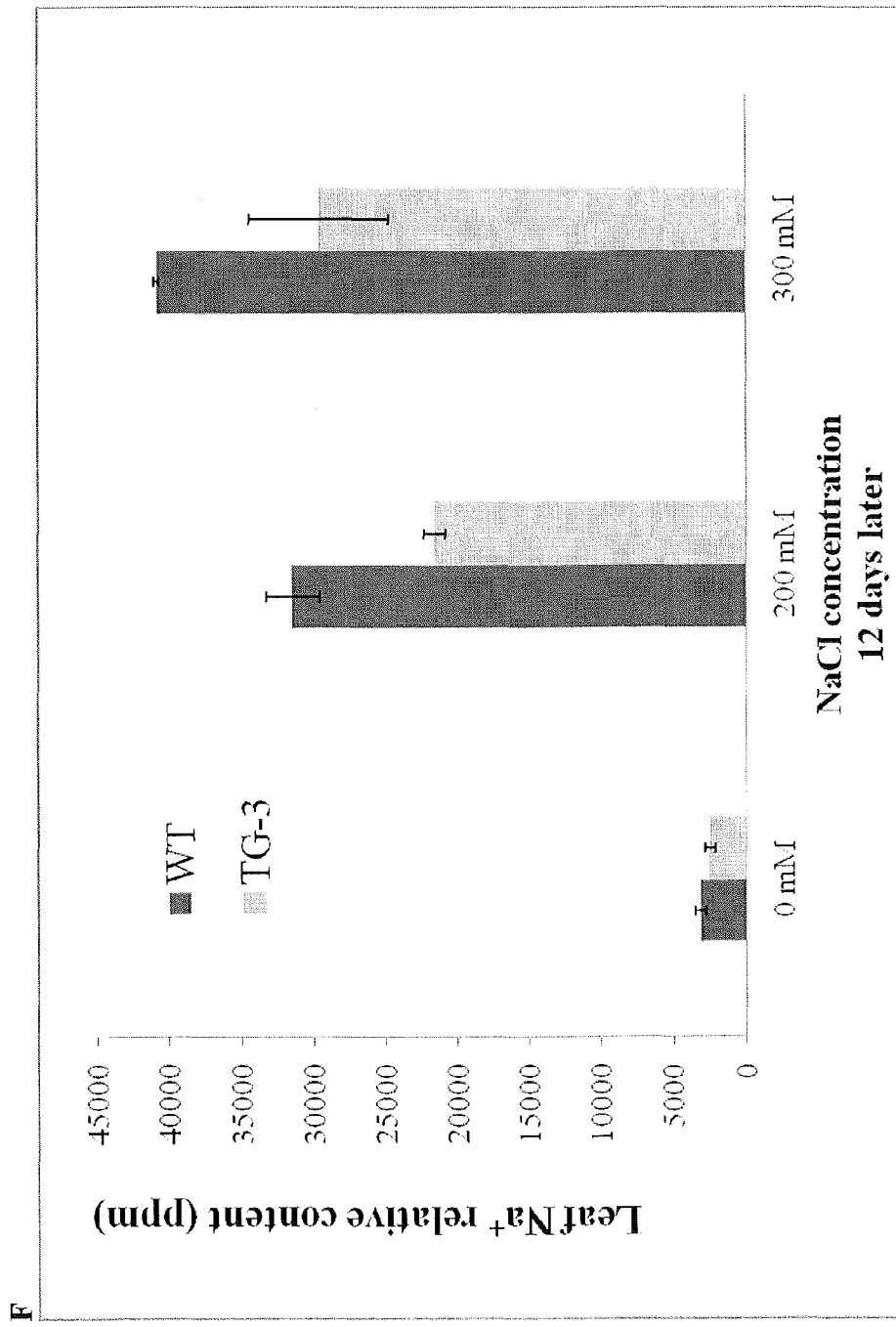

The treated plants were also tested for their ability to recover from salt stress by treatment with water with fertilizer only (i.e., no NaCl) for twelve days. As shown in FIG. 4C observations on the 12th day showed that TG plants recovered much faster and more fully than WT plants.

Relative leaf water content was also measured. Relative leaf water content between WT and TR plants was determined to be the same before the salt stress treatments; however, following exposure to 200 mM and 300 mM NaCL, TR plants exhibited higher leaf relative water contents (FIG. 4D).

To investigate cell membrane damage, we measured the leaf electrolyte leakage (EL) of leaf cells in both the transgenic and WT plants grown under normal and saline conditions. No significant difference was observed in cell EL between the TG plants and the WT kept under normal conditions (no NaCl) (FIG. 4E). In contrast, the difference became pronounced when 200 mM and 300 mM NaCl were applied to plants (FIG. 4E). Although the leaf ion leakage increased with increasing concentration of NaCl in both TG and WT plants, it was still significantly higher in WT control plants than in the TG plants (FIG. 4E).

The amount of Na+ in the shoots of WT plants and TG plants was also measured. Under normal growth conditions (i.e., no NaCl), there was no significant difference in Na+ content between the shoots of the WT and TG (FIG. 4F). However, the levels of Na+ in the shoots of WT plants following the NaCl treatments resulted in a significantly higher accumulation of Na+ as compared with the TR plants (FIG. 4F). Without being bound to any particular theory, this result may indicate that the enhanced salt tolerance in TG plants may be due to a reduction of Na+ toxicity resulting from a reduced uptake of Na+.

Overall, these results demonstrate that overexpressing Osmir319 gene leads to increased salt tolerance in turfgrass plants.

Figure 5:
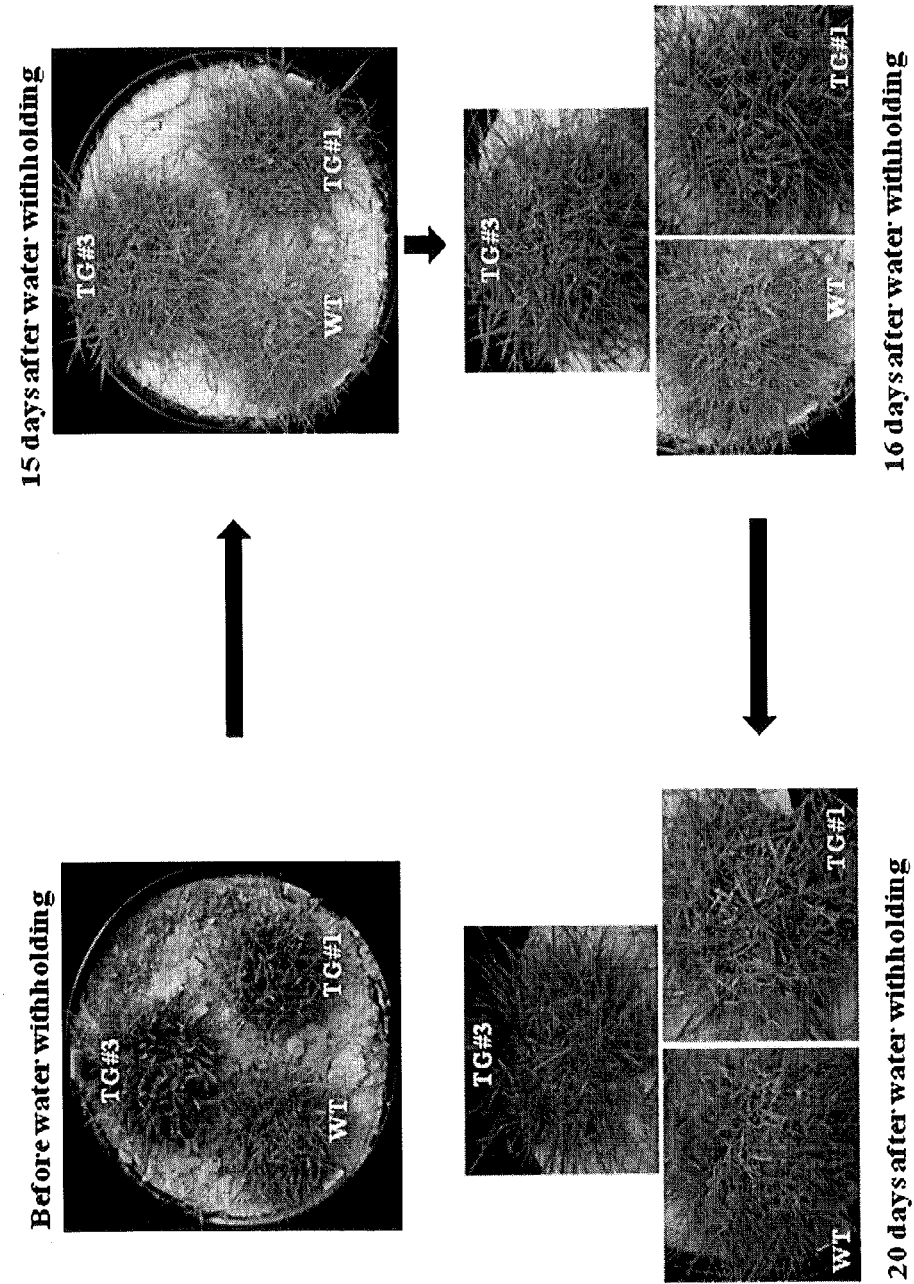
FIGS. 5A-5C show the response of WT and TG plants to drought stress.
Figure 5:
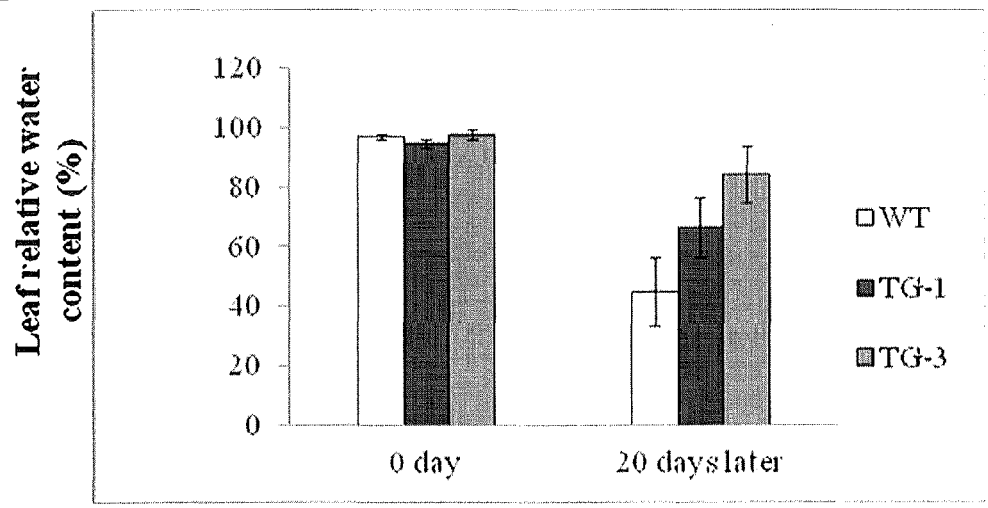
Figure 5:
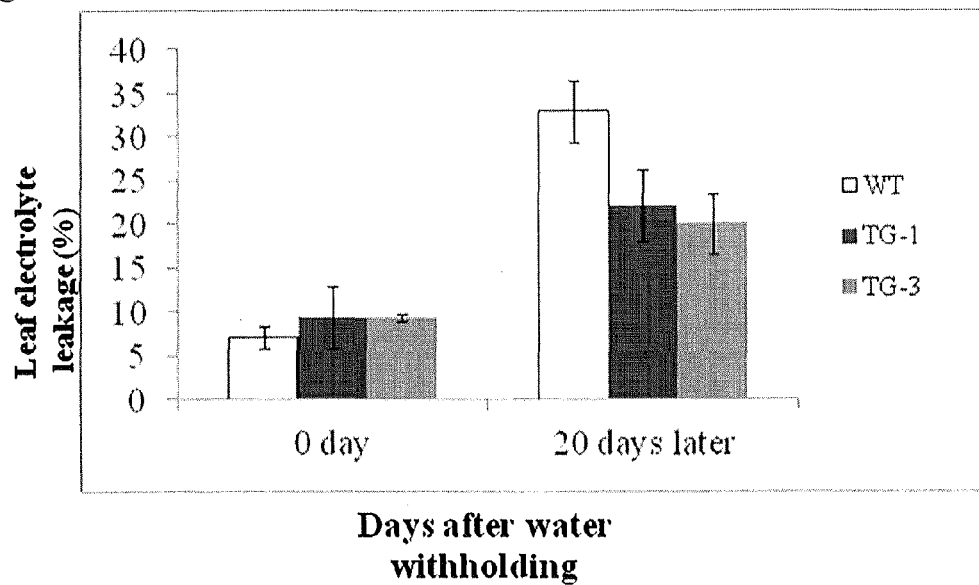

Example 10. Over-Expression of Os_miR319 Results in Enhanced Drought Tolerance in TG Creeping Bentgrass To test whether over-expression of mir319 can confer drought tolerance, TR and WT plants were subjected to drought stress for 20 days as described in Example 5. As shown in FIG. 5A, WT plants showed obvious dehydration symptoms, including turgor loss and wilting. In contrast, the TR plants retained much more turgidity (FIG. 5A). The water status in WT and TG plants was also compared by measuring relative water content and electrolyte leakage (i.e., cell membrane damage) under dehydration (i.e., drought) stress. As shown in FIGS. 5B and 5C under drought conditions the TR plants maintained higher water content (RWC) and had less cell membrane damage (EC) than the WT control plants.

Figure 6:
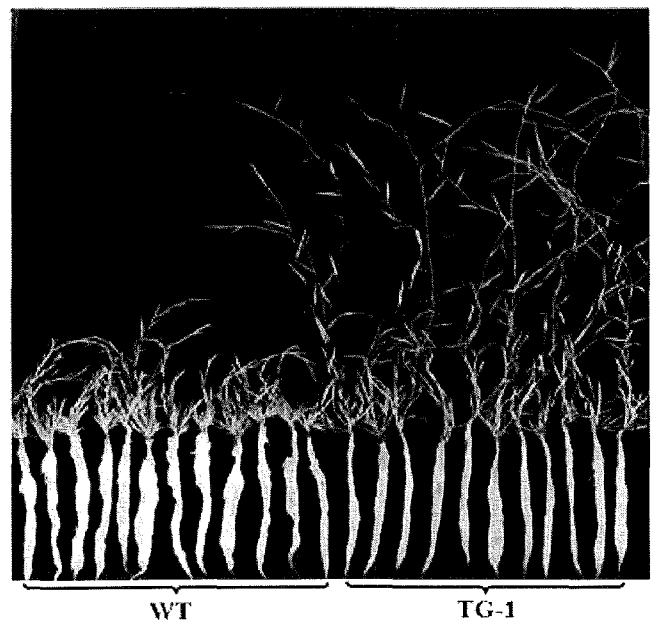
FIGS. 6A-6E show tillering and plant development of WT and TG plants under drought stress for 60 d after 30 d of normal development starting from a single tiller.
Figure 6:
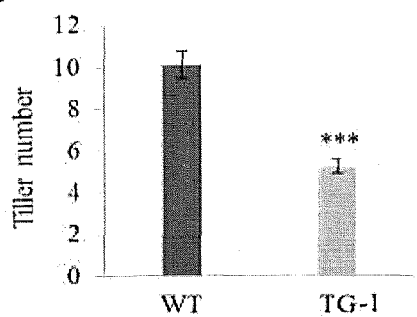
Figure 6:
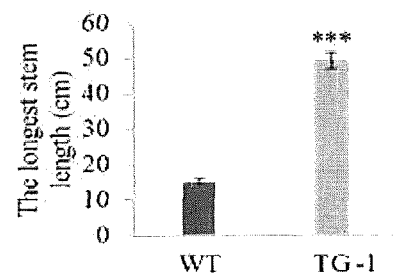
Figure 6:
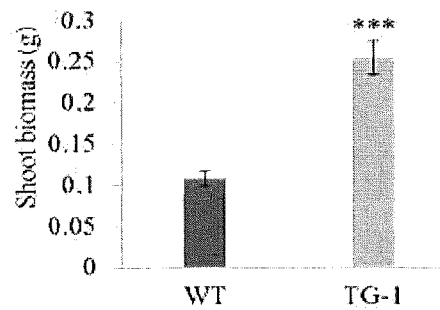
Figure 6:
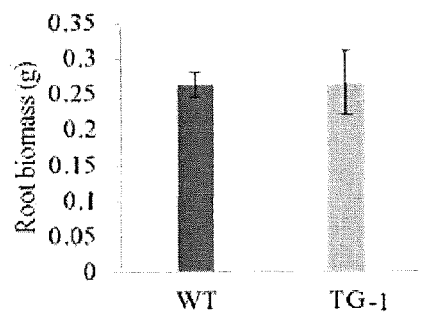

Osa-miR319a and control plants were also examined when subjected to limited water supply treatment. As exemplified in FIG. 6A, whilst the growth of control plants were completely arrested displaying severely disturbed morphology with shortened and deformed leaves and stems, Osa-miR319a plants were less impacted and continued their growth (FIG. 6A, 6C). Although the tiller number of control plants was still higher than that of Osa-miR319a transgenics (FIG. 6B), the shoot biomass of control plants was significantly reduced (FIG. 6D) in contrast with data obtained under normal growth conditions (FIG. 3C). In addition, contrary to the observation under normal growth conditions that Osa-miR319a plants had less root growth than controls (FIG. 3A, 3D), no significant difference in root biomass was observed between these plants under water deficit, indicating that root development in Osa-miR319a plants was less impacted by the stress than that in controls (FIG. 6A, 6E).

Figure 7:
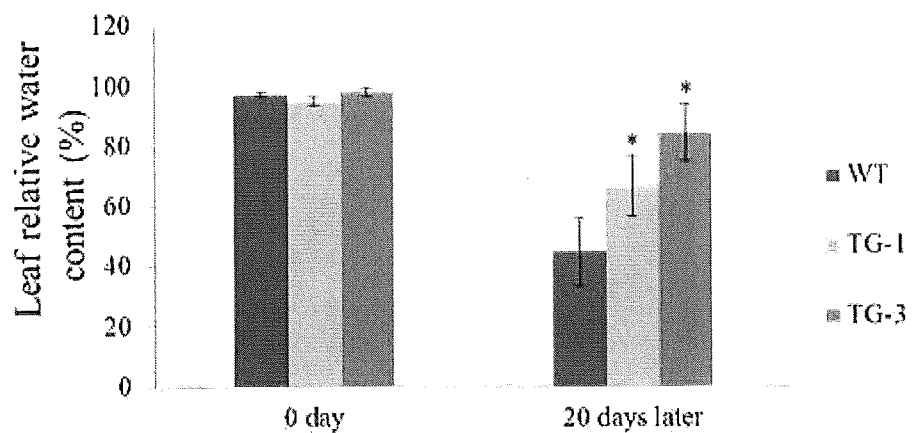
FIG. 7A-7B show leaf relative water content (RWC) and leaf electrolyte leakage (EL) of WT and TG plants under normal and drought stress conditions.
Figure 7:
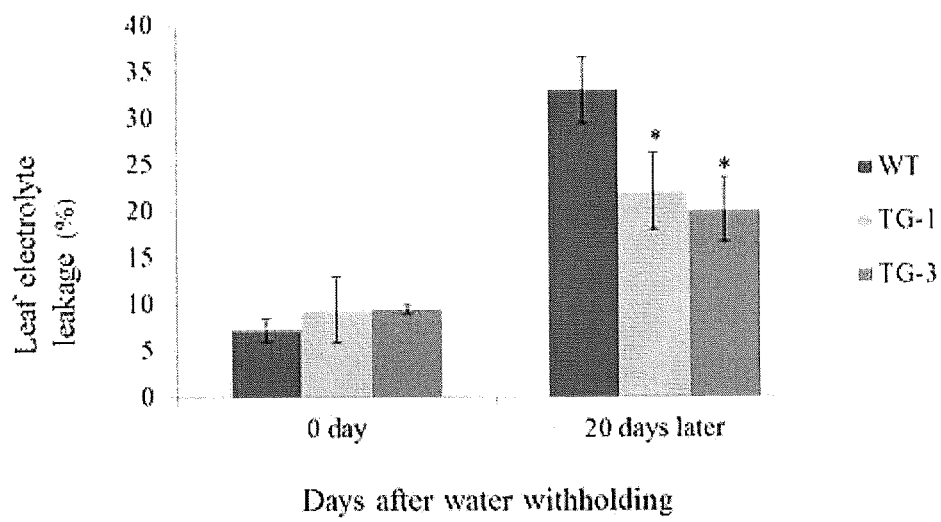
Figure 8:
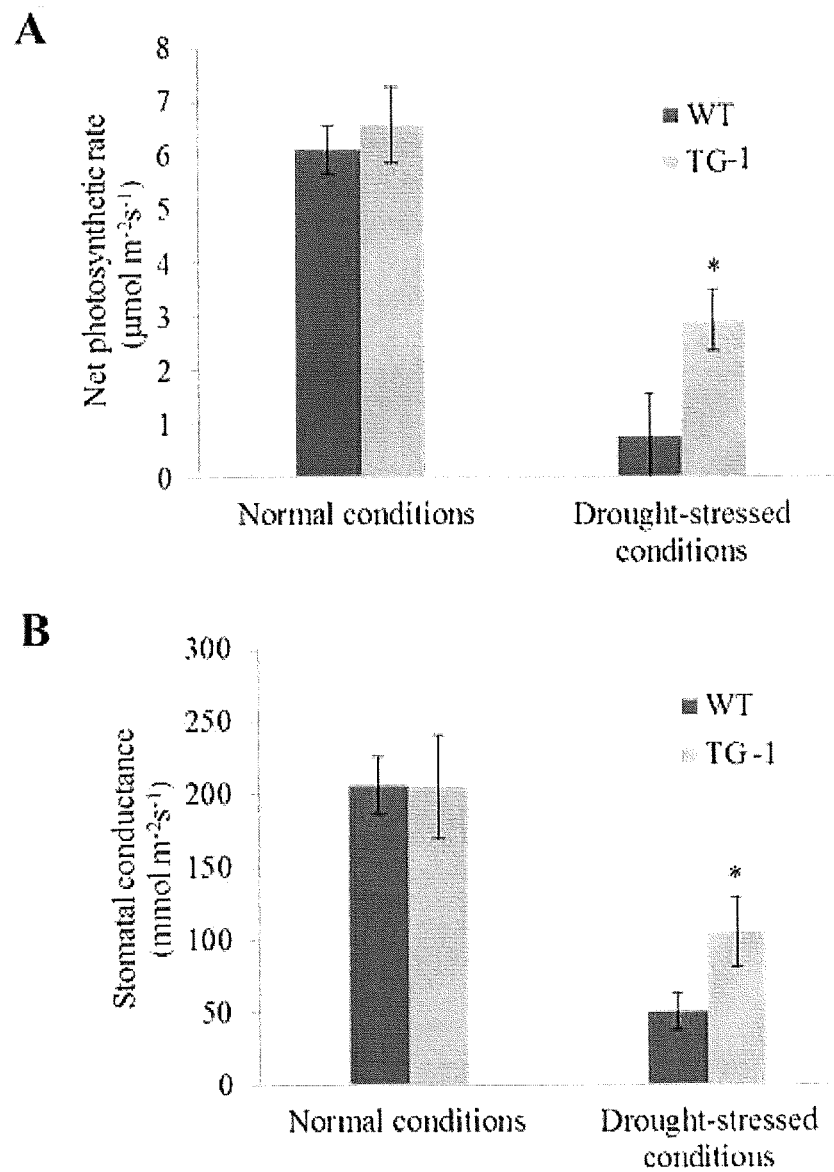
FIGS. 8A-8B show the photosynthetic characteristics of WT and a representative Osa-miR319a TG line (TG-1) measured under normal growth conditions and 5 d after dehydration stress.

Further investigation of plant water status and cell membrane integrity revealed that both control and Osa-miR319a plants had similar RWC under normal growth conditions, whereas under dehydration stress, water loss and drought-elicited cell membrane damage in Osa-miR319a plants were significantly less than that in controls (FIG. 7A, 7B) suggesting an enhanced water retention capacity and cell membrane integrity in Osa-miR319a plants. Photosynthesis is one of the primary processes affected when plants are subjected to environmental stress. An increase in stomatal conductance and maintenance of photosynthesis have been demonstrated to be positively correlated to plant performance under stress (Nelson et al. *Proc Natl Acad Sci USA* 104: 16450-16455 (2007)). Our study on Osa-miR319a transgenic and control plants revealed that under normal growth conditions, they were not significantly different in photosynthesis rate and stomatal conductance (FIG. 8A, 8B). However, when subjected to drought stress, Osa-miR319a transgenics exhibited higher stomatal conductance and photosynthesis rate than controls without Osa-miR319a (FIG. 8A, 8B).

Figure 9:
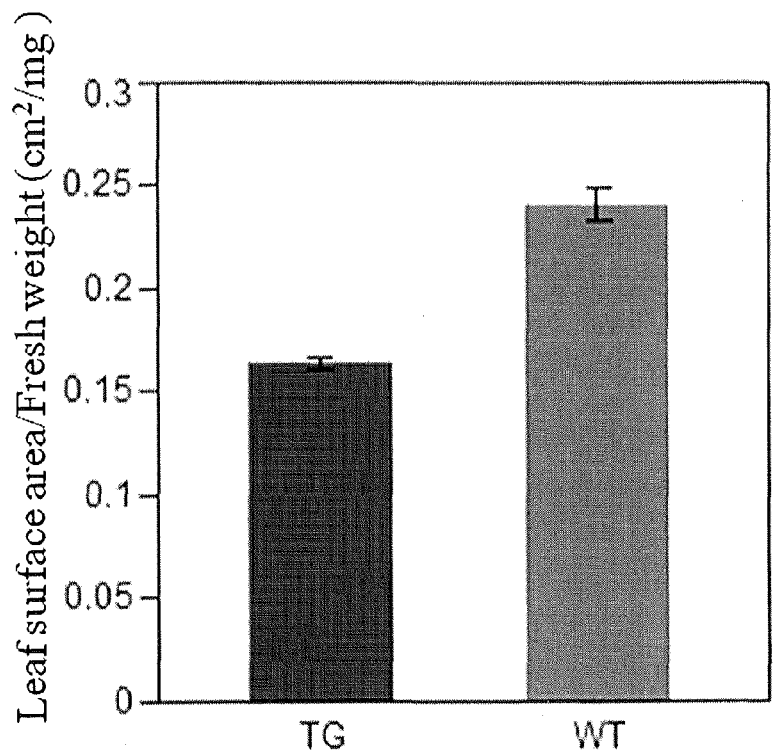
FIGS. 9A-9B show the measurement of specific leaf surface area and total wax coverage of WT and TG plants.
Figure 9:
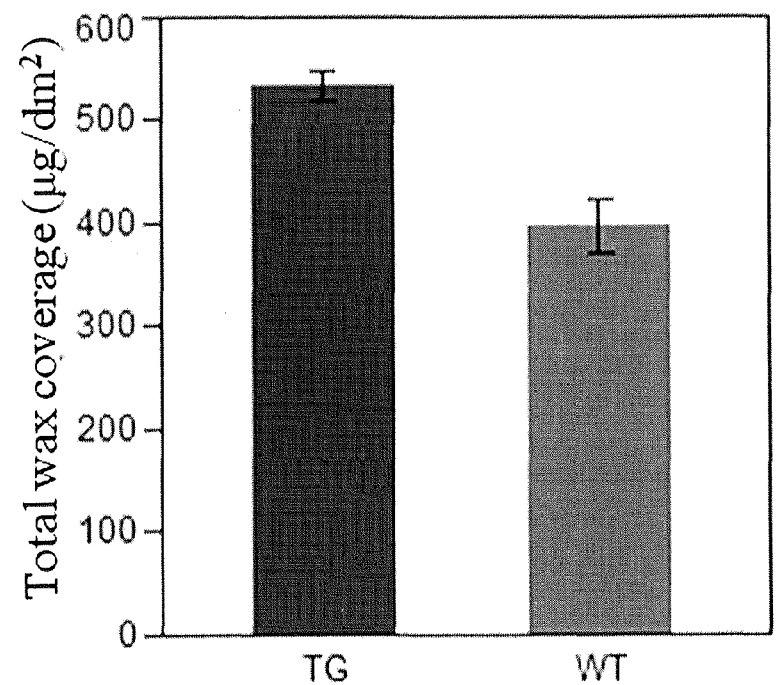

Example 11. Over-Expression of Os_miR319 Results in Decreased Specific Leaf Surface Area and Higher Accumulation of Total Wax in TG Creeping Bentgrass The specific leaf surface area (leaf surface area/fresh weight) was decreased in transgenic plants (FIG. 9A), while the leaf thickness increased (FIG. 2F). In addition, an increased accumulation of total wax was observed in TG creeping bentgrass (FIG. 9B). Wax coverage in leaf cuticle is correlated with drought tolerance. When plants are subjected with dehydration stress, the wax coverage will increase as a strategy to reduce water loss (Kosma et al. *Plant Physiology*, 151, 1918 (2009)). These changes observed in the transgenic plants may contribute to their increased drought tolerance.

Example 12. MiR319 Target Genes

Five mir319 Potential Target Genes were Down-Regulated in Transgenic Creeping Bentgrass Overexrepssing Osmir319a.

To investigate the molecular mechanism of mir319 mediated plant tolerance to abiotic stresses, the change in gene expression of potential target genes was analyzed. Using bioinformatics and experimental approaches, five potential mir319 target genes (Osa_PCF5, Osa_PCF6, Osa_PCF7, Osa_PCF8, Osa_TCP14) were characterized in rice (Yang et al., Personal Communication).

Figure 10:
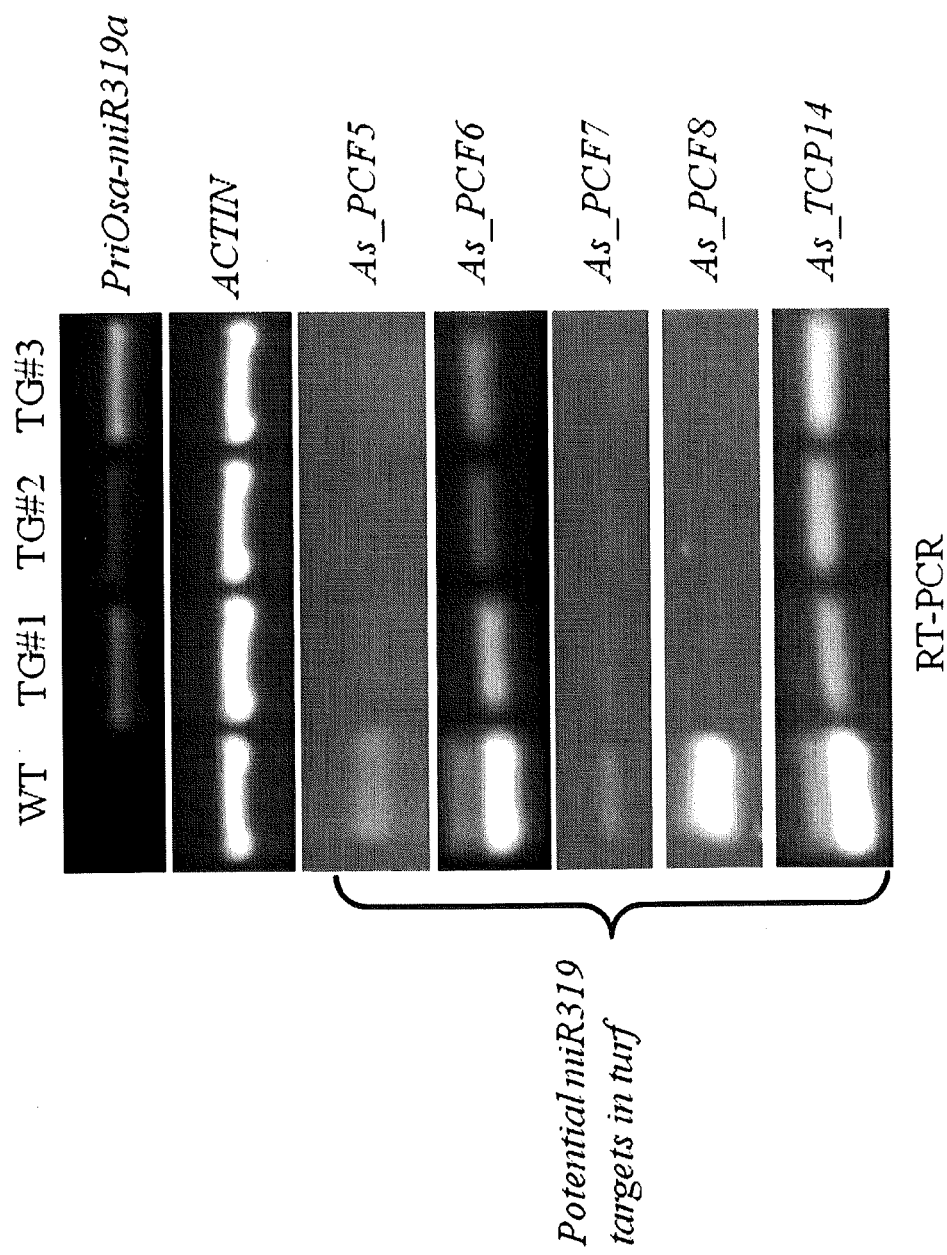
FIGS. 10A-10C show the expression levels of the five putative miR319 target genes (AsPCF5, AsPCF6, AsPCF7, AsPCF8 and AsTCP14) in WT and Osa-miR319a TG plants by semi-quantitative and real-time RT-PCR.
Figure 10:
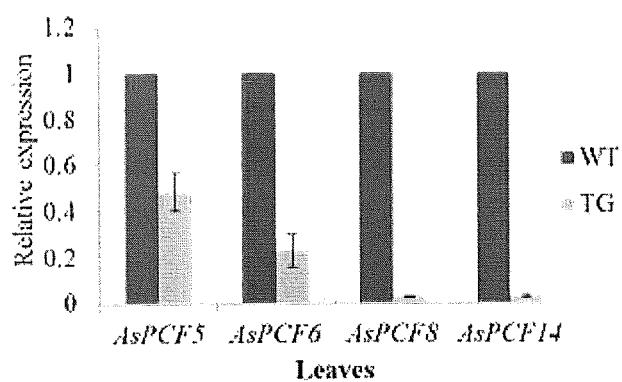
Figure 10:
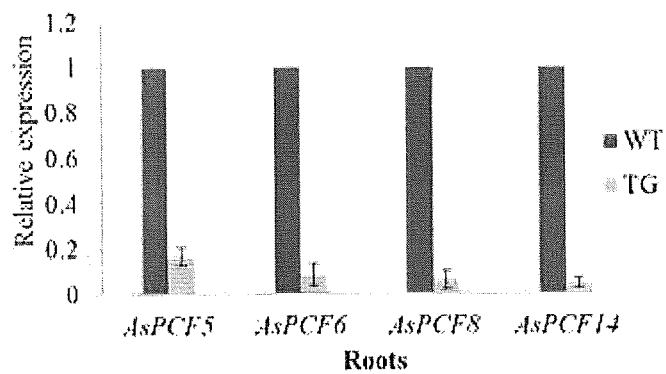

Based on the rice sequences of these potential target genes, primers were designed and the turfgrass homologues cloned. The expression of these homologues was observed in the transgenic plants. All five of the identified potential target gene homologues in turfgrass were down-regulated in transgenic plants overexpressing the rice mir319a gene (FIG. 10A) indicating that enhanced abiotic stress tolerance may be related to changes in gene expression of these five potenial target genes. Semi-quantitative and real-time RT-PCR analyses demonstrated that the putative miR319 target genes were all down-regulated in both leaves and roots of the Osa-miR319a transgenic creeping bentgrass plants (FIG. 10A-10C).

Enhanced Salt Stress Tolerance in Transgenic Plants May be Related to Down-Regulation of One Potential mir319 Target Gene, AsPCF5.

Figure 11:
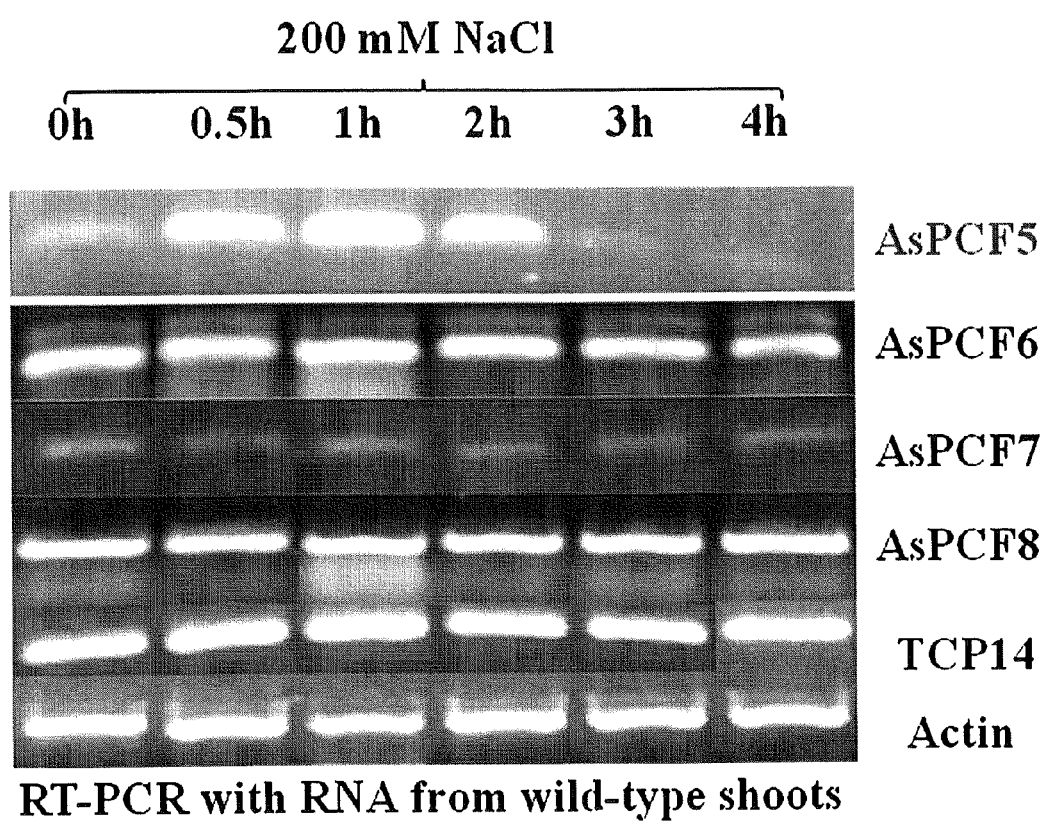
FIG. 11 shows the time course expression pattern of five putative target genes of miR319a gene in WT plants under 200 mM NaCl treatment as detected by RT-PCR.

To determine if the expression of any of the five potential target genes is regulated by salt stress WT turfgrass plants were treated with 200 mM NaCl and the level of expression for these genes observed at different time points. RT PCR analysis showed that AsPCF5 is up-regulated rapidly about after 0.5 h after beginning treatment, reaching a peak level of expression at about after 1 h after treatment, but then at about 2 h expression begins to be down-regulated (FIG. 11).

Figure 12:
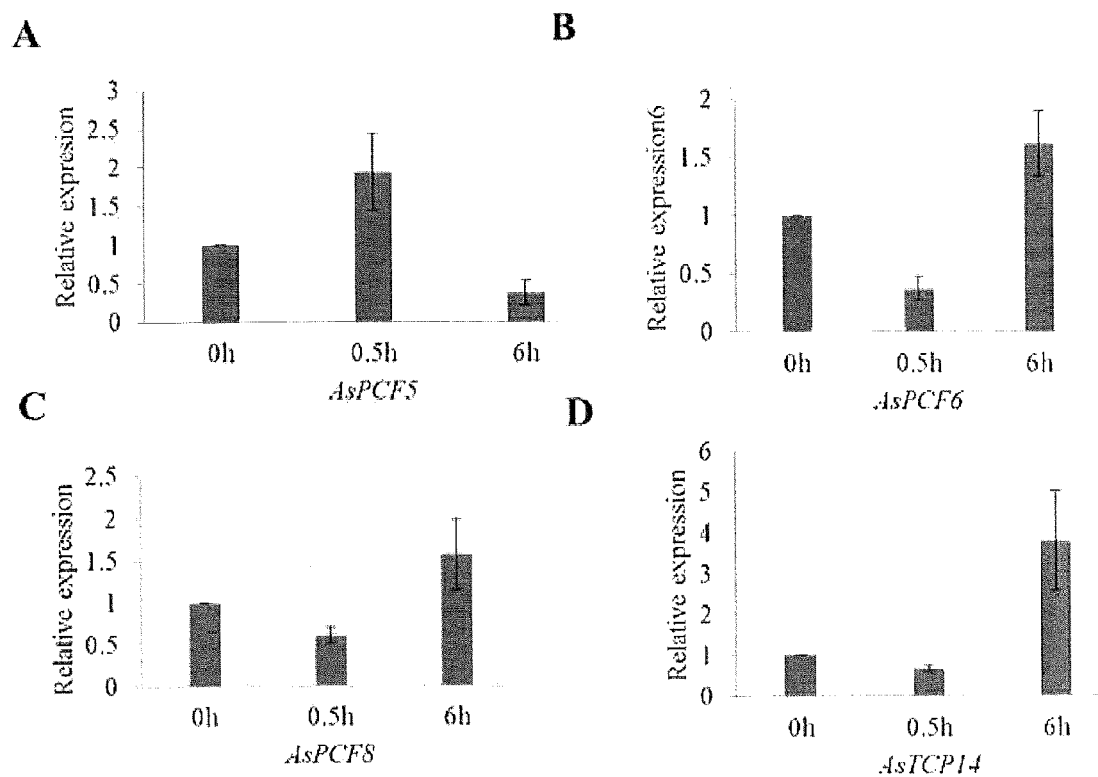
FIG. 12A-12D show the expression pattern of putative miR319 target genes in WT plants under 200 mM NaCl treatment demonstrated by Real-time RT-PCR analysis.

Real-time RT-PCR analyses showed an increase in AsPCF5 transcript 0.5 h after salinity stress, and then declined at 6 h (FIG. 12A). Real-time RT-PCR analysis also suggested a trend of up-regulation of other three putative target genes AsPCF6 (1.16 fold), AsPCF8 (1.56 fold) and AsTCP14 (3.79 fold) at 6 h after exposure to salt stress but not statistically significant (FIG. 12B-12D).

Figure 13:
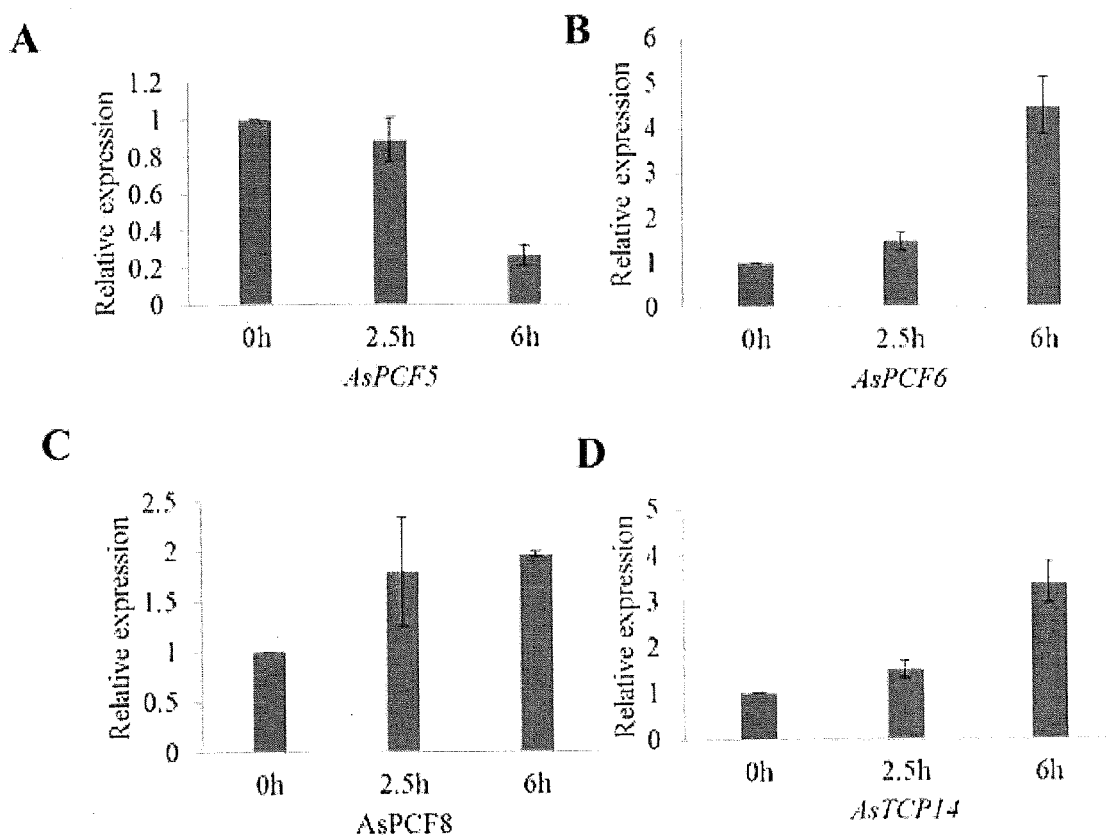
FIG. 13A-13D show the expression pattern of putative miR319 targets in creeping bentgrass plants under dehydration stress.

We then studied miR319 target TCP gene activities in response to dehydration stress. WT plants collected from pots were placed on filter paper for desiccation treatment. RNA was extracted 2.5 h and 6 h after treatment. Real-time RT-PCR results suggested that AsPCF6, AsPCF8 and AsTCP14 were all up-regulated 2.5 h after exposure to desiccation stress, but the expression level change is statistically insignificant. However, at 6-hour upon desiccation, the expressions of these three genes were all significantly up-regulated (FIG. 13B-13D).

Figure 14:
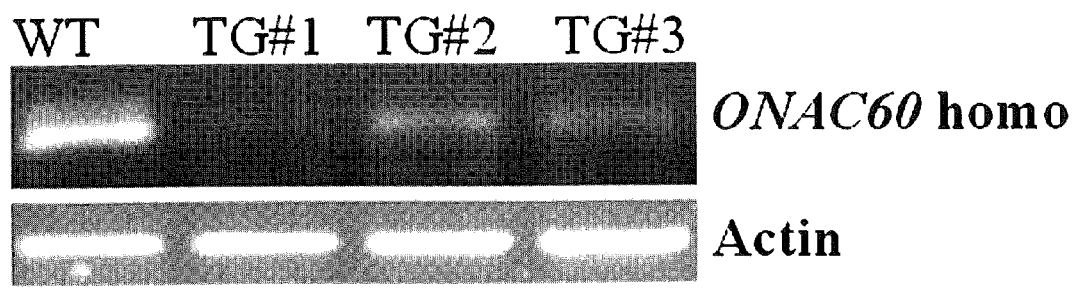
FIG. 14 shows expression levels of the ONAC60 turfgrass homolog in WT and TG plants using RT-PCR analysis.
Figure 15:
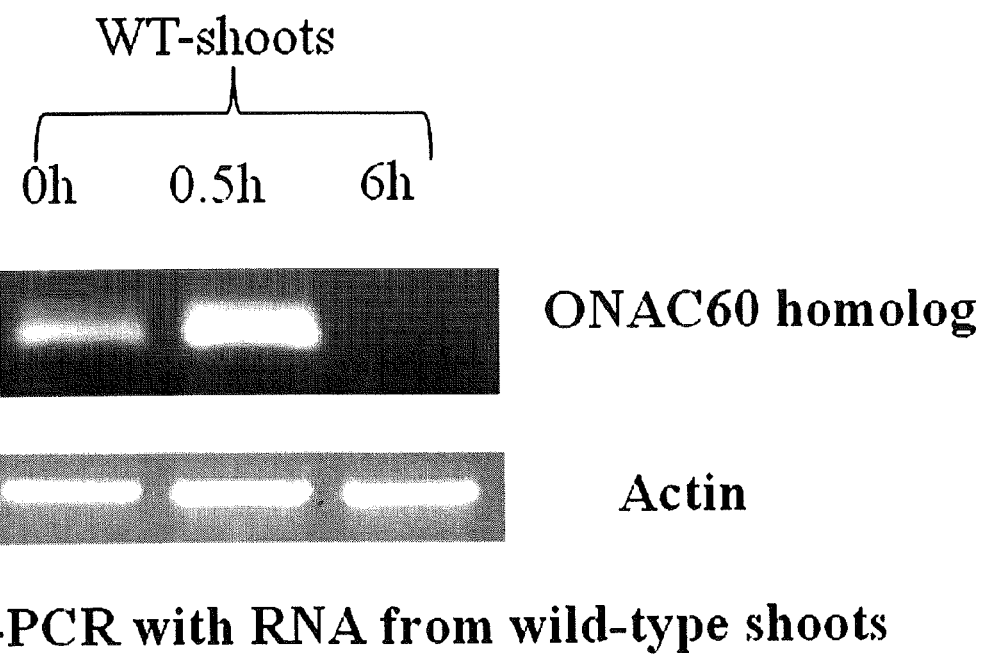
FIG. 15 shows the time course expression pattern of the ONAC60 turfgrass homolog in plants subjected to salt stress (200 mM NaCl treatment) using RT-PCR analysis.

To examine how other stress-related genes are affected in Osa-miR319a transgenic plants, we studied a transcription factor gene AsNAC60, homolog of the rice NAC-like gene ONAC60 (Os12g41680) whose expression has been shown to be dramatically impacted by overexpression of Osa-miR319. ONAC60 has been known to be the target gene of miR164 in rice, and in *Arabidopsis*, TCP genes regulate miR164 expression. Expression of the ONAC60 turfgrass homolog in WT and TG plants using RT-PCR analysis is shown in FIG. 14 and FIG. 15 shows the time course expression pattern of the ONAC60 turfgrass homolog in plants subjected to salt stress (200 mM NaCl treatment) using RT-PCR analysis.

Figure 16:
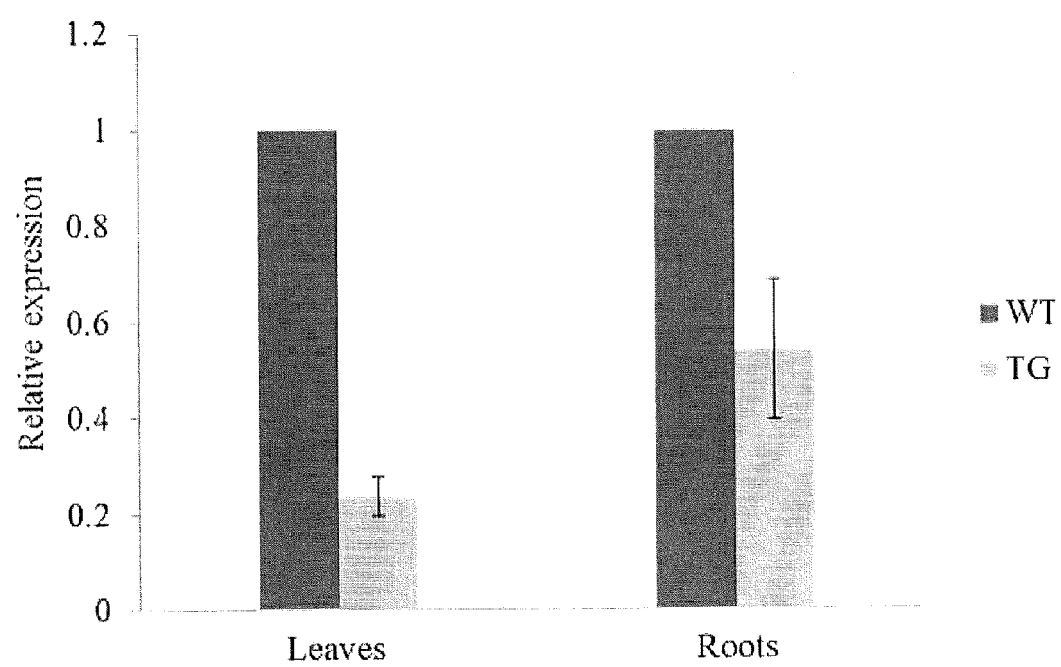
FIG. 16 shows expression levels of AsNAC60 in WT and TG plant leaves and roots. (real-time RT-PCR analysis). The ΔΔCt method was used for real-time RT-PCR analysis. Three biological replicates and three technical replicates for each biological replicate were used for data analysis. ACTIN was used as the endogenous control. Error bars indicate ±SE (n=9).
Figure 17:
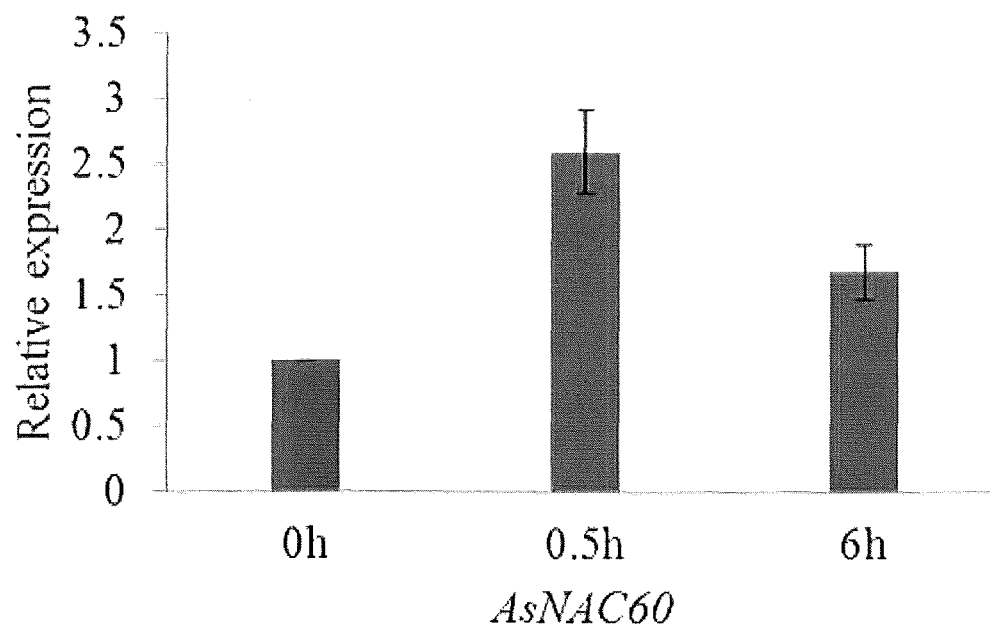
FIG. 17 shows a time course expression pattern of AsNAC60 under 200 mM NaCl treatment. Real time RT-PCR analysis of AsNAC60 in WT plant leaves at three time points 0 h, 0.5 h and 6 h after treatment with 200 mM NaCl. The ΔΔCt method was used for real-time RT-PCR analysis. ACTIN was used as an endogenous control. Error bars indicate ±SE (n=3 technical replicates).

Further, to test whether overexpression of miR319 can impact ONAC60 in turfgrass potentially through TCP-mediated miR164 regulation pathway, a partial sequence of the AsNAC60 cDNA (JX570756) was cloned from creeping bentgrass. This partial sequence was found to be highly homologous to ONAC60. Real-time RT-PCR analyses demonstrated that AsNAC60 expression was down-regulated in Osa-miR319a transgenic creeping bentgrass plants in both leaves and roots (FIG. 16), indicating that miR319 indeed indirectly regulates AsNAC60 expression. FIG. 17 shows the time course expression pattern of the AsNAC60 in plants subjected to salt stress (200 mM NaCl treatment) using RT-PCR analysis. A significant increase in AsNAC60 expression level at time point 0.5 h (2.5 fold) was revealed as well as a significant decrease at time point 6 h (1.67 fold).

Example 13. Antisense

Utilizing the known rice nucleotide sequence, primers were prepared and used to successfully amplify an 859-bp DNA fragment of the AsPCF5 homolog from creeping bentgrass through PCR (see SEQ ID NO:4). Such techniques are known to those skilled in the art. See, e.g., Sambrook et al., Molecular Cloning: A Laboratory Manual 2nd Ed. (Cold Spring Harbor, N.Y., 1989); Ausubel et al.

Current Protocols in Molecular Biology (Green Publishing Associates, Inc. and John Wiley & Sons, Inc., New York).

Figure 18:
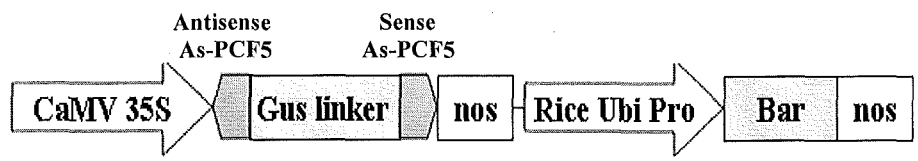
FIG. 18 shows an RNAi construct comprising portions of the creeping bentgrass nucleotide sequence encoding PCF5.

To produce transgenic plants in which AsPCF5 is downregulated, an RNAi construct can be prepared in which a portion of sense and a portion of anti-sense creeping bentgrass AsPCF5 (from about 21 nt to about 859 nt in length) are linked to one another by, for example, a GUS fragment (See, as a representative embodiment, FIG. 18) and/or an intron sequence (e.g., intron-2 from the Pdk gene of Flayeria8 and/or intron-1 from the *Arabidopsis* Fad2 gene (Smith et al. "Gene expression: Total silencing by intron-spliced hairpin RNAs." Nature 407(6802):319-320 (2000)). The construct can then be introduced into a plant via any method known for transforming a plant, for example, *Agrobacterium* transformation. It is expected that transformed creeping grass plants comprising such RNAi constructs will have increased tolerance to abiotic stress. Plant species in addition to creeping bentgrass may be transformed using the RNAi constructs comprising antisense and sense portions of the creeping bentgrass AsPCF5 gene and tested for increased tolerance to abiotic stress.

In addition, the high level of nucleic acid homology among the AsPCF5 homologs from different species should allow the isolation of nucleotide sequences encoding AsPCF5 from many other plant species, and thus the preparation of further constructs useful for increasing abiotic stress tolerance in many additional plant species.

What is claimed is:

1. A transgenic plant having increased tolerance to drought, the plant comprising a recombinant nucleic acid molecule, said recombinant nucleic acid molecule comprising a nucleotide sequence encoding miR319 operatively associated with a promoter, wherein overexpression of the nucleotide sequence encoding miR319 confers increased tolerance to drought, and wherein the nucleotide sequence encoding miR319 is the nucleotide sequence of SEQ ID NO: 1, the nucleotide sequence of SEQ ID NO: 7, and/or the nucleotide sequence of SEQ ID NO: 8.

2. A method of producing a transgenic plant having increased tolerance to drought, the method comprising:
   a) transforming a plant cell with a recombinant nucleic acid molecule, wherein said recombinant nucleic acid molecule comprises
      a nucleotide sequence encoding miR319 operatively associated with a promoter, wherein the nucleotide sequence encoding miR319 is the nucleotide sequence of SEQ ID NO: 1, the nucleotide sequence of SEQ ID NO: 7, and/or the nucleotide sequence of SEQ ID NO: 8; and
   (b) regenerating a transgenic plant from the transformed plant cell, thereby producing a transgenic plant having increased tolerance to drought.

3. A transgenic plant having increased tolerance to drought produced by the method of claim 2.

4. A seed of the transgenic plant of claim 1, wherein the seed comprises said recombinant nucleic acid molecule in its genome.

5. A seed of the transgenic plant of claim 3, wherein the seed comprises said recombinant nucleic acid molecule in its genome.

6. A crop comprising a plurality of transgenic plants of claim 1, planted together in an agricultural field, a golf course, a residential lawn, a road side, an athletic field, and/o a recreational field.

7. A crop comprising a plurality of transgenic plants of claim 3, planted together in an agricultural field, a golf course, a residential lawn, a road side, an athletic field, and/or a recreational field.

* * * * *